United States Patent

Oberdorf et al.

Patent Number: 5,358,968
Date of Patent: Oct. 25, 1994

[54] SUBSTITUTED OXIME ETHERS, THEIR PREPARATION AND THEIR USE FOR CONTROLLING PESTS AND FUNGI

[75] Inventors: Klaus Oberdorf, Heidelberg; Hubert Sauter, Mannheim; Wassilios Grammenos, Ludwigshafen; Reinhard Kirstgen, Neustadt; Volker Harries, Frankenthal; Gisela Lorenz, Neustadt; Eberhard Ammermann, Heppenheim; Randall E. Gold, Wachenheim; Wolfgang Siegel, Mannheim; Albrecht Harreus, Ludwigshafen, all of Fed. Rep. of Germany

[73] Assignee: BASF Aktiengesellschaft, Ludwigshafen, Fed. Rep. of Germany

[21] Appl. No.: 91,254

[22] Filed: Jul. 15, 1993

[30] Foreign Application Priority Data

Jul. 15, 1992 [DE] Fed. Rep. of Germany ....... 4223210
Sep. 30, 1992 [DE] Fed. Rep. of Germany ....... 4232816
Mar. 31, 1993 [DE] Fed. Rep. of Germany ....... 4310495

[51] Int. Cl.$^5$ ................. A61K 31/165; C07C 251/38
[52] U.S. Cl. .................... 514/620; 514/357; 514/438; 514/521; 514/522; 514/539; 514/619; 546/300; 549/77; 558/391; 558/404; 558/414; 564/164; 564/165
[58] Field of Search ............... 564/164, 165; 514/620, 514/357, 438, 539, 521, 522, 619; 546/300; 549/77; 558/391, 404, 414

[56] References Cited

U.S. PATENT DOCUMENTS 5,166,399 11/1992 Schuetz ................. 560/35
5,194,662 3/1993 Brand et al. ............ 560/35

FOREIGN PATENT DOCUMENTS 0253213 1/1988 European Pat. Off. .
463488 1/1992 European Pat. Off. .

*Primary Examiner*—Peter O'Sullivan
*Attorney, Agent, or Firm*—Oblon, Spivak, McClelland, Maier & Neustadt

[57] ABSTRACT

Substituted oxime ethers of the general formula I

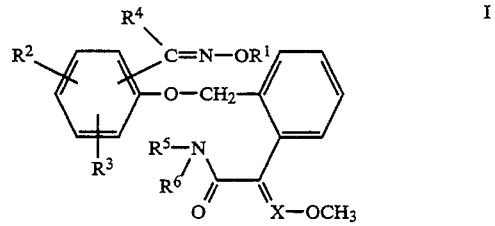

where $R^1$ is alkyl, alkenyl, alkynyl, haloalkyl, haloalkenyl, alkoxyalkyl, cycloalkyl, cycloalkylalkyl, cyanoalkyl, alkoxycarbonylalkyl, arylalkyl, heteroarylalkyl, arylalkenyl or aryloxyalkyl, the aromatic or heteroaromatic ring being substituted or unsubstituted, $R^2$ and $R^3$ are hydrogen, alkyl, haloalkyl, alkoxy, haloalkoxy, halogen, cyano or nitro, $R^4$ is hydrogen, alkyl, cycloalkyl, haloalkyl or aryl, the aromatic ring being substituted or unsubstituted, and $R^5$ and $R^6$ are identical or different and each is hydrogen or alkyl, and X is CH or N, and fungicides and pesticides containing these compounds.

8 Claims, No Drawings

SUBSTITUTED OXIME ETHERS, THEIR PREPARATION AND THEIR USE FOR CONTROLLING PESTS AND FUNGI

The present invention relates to novel substituted oxime ethers of the general formula I

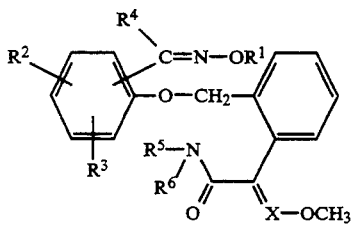

where

R$^1$ is C$_1$-C$_6$-alkyl, C$_3$-C$_6$-alkenyl, C$_3$-C$_4$-alkynyl, C$_1$-C$_6$-haloalkyl, C$_3$-C$_6$-haloalkenyl, C$_1$-C$_4$-alkoxy-C$_1$-C$_4$-alkyl, C$_3$-C$_6$-cycloalkyl, C$_3$-C$_6$-cycloalkyl-C$_1$-C$_4$-alkyl, cyano-C$_1$-C$_6$-alkyl, C$_1$-C$_6$-alkoxycarbonyl-C$_1$-C$_6$-alkyl, aryl-C$_1$-C$_6$-alkyl, hetaryl-C$_1$-C$_6$-alkyl, aryl-C$_3$-C$_6$-alkenyl or aryloxy-C$_1$-C$_6$-alkyl, where the aromatic or heteroaromatic ring is unsubstituted or substituted by one or more of the following radicals: C$_1$-C$_4$-alkyl, C$_1$- or C$_2$-haloalkyl, C$_3$-C$_6$-cycloalkyl, C$_1$-C$_4$-alkoxy, C$_1$ or C$_2$-haloalkoxy, halogen, aryl or aryloxy, R$^2$ and R$^3$ are identical or different and are each hydrogen, C$_1$-C$_4$-alkyl, C$_1$- or C$_2$-haloalkyl, C$_1$-C$_4$-alkoxy, C$_1$- or C$_2$-haloalkoxy, halogen, cyano or nitro, R$^4$ is hydrogen, C$_1$-C$_6$-alkyl C$_3$-C$_6$-cycloalkyl, C$_1$-C$_2$-haloalkyl or aryl, where the aromatic ring is unsubstituted or substituted by one or more of the following radicals: C$_1$-C$_4$-alkyl, C$_1$- or C$_2$-haloalkyl, C$_1$-C$_4$-alkoxy, C$_1$- or C$_2$-haloalkoxy, halogen, cyano or nitro, R$^5$ and R$^6$ are identical or different and are each hydrogen or C$_1$-C$_4$-alkyl and X is CH or N.

The invention also relates to methods and intermediates for producing compounds I, fungicides containing them, and their use, pesticides containing them, and the use of compounds of the general formula IA

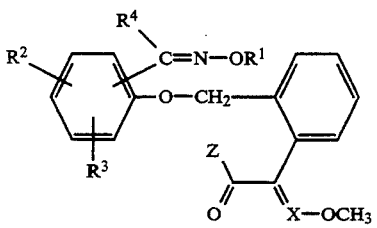

where R$^1$, R$^2$, R$^3$, R$^4$ and X have the meanings given in claim 1 and Z is NR$^5$R$^6$ or OR$^7$, where R$^5$ and R$^6$ have the above meanings and R$^7$ is C$_1$-C$_4$-alkyl, for controlling pests.

It is known that oxime ethers, for example methyl 2-(2'-methylphenoxymethyl)-phenylglyoxylate O-methyl oxime or methyl 2-(2'-methyl-4'-(methoximinoeth-1''-yl)phenoxymethyl)-phenylglyoxylate O-methyl oxime, can be used as fungicides (European Patents 253,213, 386,561 and 398,692).

Further, EP-A 386 561 discloses compounds of the formula IA, Z being methoxy, as fungicidal active ingredients.

It is an object of the invention to provide novel compounds having improved and wider applicability in crop protection.

We have found that this object is achieved by compounds I defined at the outset, methods and intermediates for producing them, agents containing them and the use thereof for controlling fungi, and agents for controlling fungi and the use of compounds of the formula IA defined at the outset for controlling fungi.

In the general formulae I and IA,

R$^1$ may be, for example, C$_1$-C$_6$-alkyl (C$_1$-C$_4$-alkyl) (e.g. methyl, ethyl, n-propyl, isopropyl, n-butyl, isobutyl, sec-butyl, tert-butyl, n-pentyl, isopentyl, sec-pentyl, tert-pentyl, neopentyl or hexyl), C$_3$-C$_6$-alkenyl (e.g. allyl, 2-butenyl, 3-butenyl, 1-methyl-2-propenyl or 2-methyl-2-propenyl), C$_3$- or C$_4$-alkynyl (e.g. propargyl or 2-butynyl), C$_1$-C$_6$-haloalkyl (e.g. 2-fluoroethyl), C$_3$-C$_6$-haloalkenyl (e.g. 3-chloroallyl), C$_1$-C$_4$-alkoxy-C$_1$-C$_6$-alkyl (e.g. 2-methoxyethyl or 3-ethoxypropyl), C$_3$-C$_6$-cycloalkyl (e.g. cyclopropyl, cyclobutyl, cyclopentyl or cyclohexyl), C$_3$-C$_6$-cycloalkyl-C$_1$-C$_4$-alkyl (e.g. cyclopropylmethyl or cyclohexylmethyl), cyano-C$_1$-C$_6$-alkyl (e.g. cyanomethyl or 3-cyanopropyl), C$_1$-C$_6$-alkoxycarbonyl-C$_1$-C$_6$-alkyl (e.g. ethoxycarbonylmethyl, tert-butoxycarbonylmethyl or tert-butoxycarbonylpropyl), aryl-(phenyl)-C$_1$-C$_6$-alkyl (e.g. benzyl, 2-phenylethyl, 3-phenylpropyl or 4-phenylbutyl), hetaryl-(pyridyl, thienyl) -C$_1$-C$_6$-alkyl (e.g. pyrid-3-ylmethyl or thien-2-ylmethyl), aryl-(phenyl) -C$_3$-C$_6$-alkenyl (e.g. 4-phenyl-2-butenyl or 4-phenyl-3-butenyl), or aryloxy-(phenoxy)-C$_1$-C$_6$-alkyl (e.g. phenoxymethyl, phenoxyethyl, phenoxypropyl, phenoxybutyl, naphthyloxymethyl or naphthyloxyethyl), where the aromatic (phenyl) or heteroaromatic (pyridyl, thienyl) ring is unsubstituted or substituted by one or more, for example 1 to 5, in particular 1 to 3, of the following radicals:

C$_1$-C$_4$-alkyl (e.g. methyl, ethyl, propyl or butyl), C$_1$- or C$_2$-haloalkyl (e.g. trifluoromethyl or trichloromethyl), C$_3$-C$_6$-cycloalkyl (e.g. cyclopropyl, cyclobutyl, cyclopentyl or cyclohexyl), C$_1$-C$_4$-alkoxy (e.g. methoxy, ethoxy, propoxy or butoxy), C$_1$- or C$_2$-haloalkoxy (e.g. trifluoromethoxy), halogen (e.g. fluorine, chlorine or bromine), aryl (e.g. phenyl) or aryloxy (e.g. phenoxy), R$^2$ and R$^3$ may be identical or different and are each hydrogen, C$_1$-C$_4$-alkyl (e.g. methyl, ethyl, n-propyl, isopropyl or butyl), C$_1$- or C$_2$-haloalkyl (e.g. trifluoromethyl or trichloromethyl), C$_1$-C$_4$-alkoxy (e.g. methoxy, ethoxy, n-propoxy, isopropoxy or butoxy), C$_1$- or C$_2$-haloalkoxy (e.g. trifluoromethoxy), halogen (e.g. fluorine, chlorine, bromine or iodine), cyano or nitro, R$^4$ may be, for example, C$_1$-C$_6$-alkyl, (C$_1$-C$_4$-alkyl) (e.g. methyl, ethyl, n-propyl, isopropyl, n-butyl, isobutyl, sec-butyl, tert-butyl, n-pentyl, isopentyl, sec-pentyl, tert-pentyl, neopentyl or hexyl) or aryl (e.g. phenyl), where the aromatic ring is unsubstituted or substituted by one or more, for example 1 to 5, in particular 1 to 3, of the following radicals:

C$_1$-C$_4$-alkyl (e.g. methyl, ethyl, propyl or butyl), C$_1$- or C$_2$-haloalkyl (e.g. trifluoromethyl or trichloromethyl), C$_1$-C$_4$-alkoxy (e.g. methoxy, ethoxy, propoxy or butoxy), $C_1$- or $C_2$-haloalkoxy (e.g. difluoromethoxy or trifluoromethoxy), halogen (e.g. fluorine, chlorine, bromine or iodine), cyano or nitro, $R^5$ and $R^6$ may be identical or different and are each hydrogen or $C_1$-$C_4$-alkyl (e.g. methyl, ethyl, n-propyl, isopropyl or butyl), preferred compounds being those in which $R^5$ is hydrogen and $R^6$ is methyl, X may be CH or N, and $R^7$ may be $C_1$-$C_4$-alkyl as mentioned above, especially methyl.

—$C(R^4)$=N—O—$R^1$ may be in the 2-, 3- or, preferably, 4-position on the phenyl radical relative to —O—$CH_2$—.

Owing to the C=C or C=N double bonds, the novel compounds of the general formula I and IA may be obtained in the preparation as E/Z isomer mixtures. These may be separated into the individual components in a conventional manner, for example by crystallization or chromatography. Both the individual isomeric compounds and mixtures thereof are embraced by the invention and can be used as fungicides and pesticides. Regarding the group —$C(CONR^5R^6)$=X—$OCH_3$, preferred compounds are those in which $CONR^5R^6$ and $OCH_3$ at the C=X double bond have the E configuration. Regarding the group —$C(R^4)$=N—$OR^1$, preferred compounds are those in which $R^4$ and $OR^1$ on the C=N double bond have the cis configuration and in which the C=N double bond therefore has the E configuration in the case of small substituents, e.g. methyl.

The novel compounds of the formula I are prepared, for example, by reacting a substituted oxime ether of the general formula II, where L is $C_1$-$C_4$-alkoxy, hydroxyl or halogen, such as chlorine or bromine, with a primary or secondary amine of the formula $HNR^5R^6$.

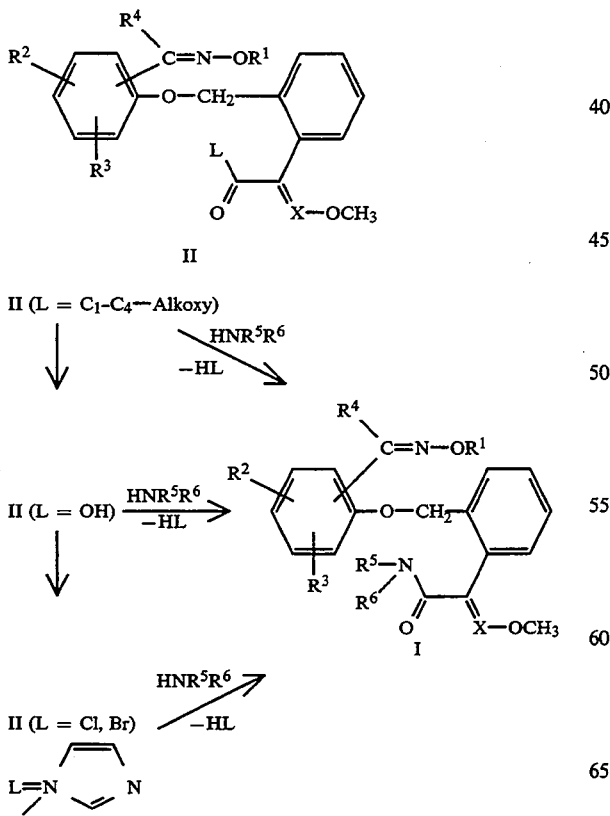

Compounds of the formula II where L is $C_1$-$C_4$-alkoxy are disclosed in European Patent 386,561 or can be prepared by processes similar to those described there. The corresponding carboxylic acids II (L=OH) can be readily prepared therefrom by conventional processes (cf. for example Houben-Weyl, Vol. E 5, pages 223–254; Org. Reactions 24 (1976), 187–224). These can then be converted into activated carboxylic acid derivatives, examples being imidazolides II in which n is imidazol-1-yl or the acyl halides II in which n is Cl or Br (cf. for example Houben-Weyl, Vol. VIII, page 463 et seq.). Reaction of the compounds of the formula II with primary or secondary amines $HNR^5R^6$ gives the corresponding amides of the general formula I (cf. for example Houben-Weyl, Vol. E 5, pages 941–977 and 983–991; Houben Weyl, Vol. VIII, page 654 et seq.).

$R^1$, $R^2$, $R^3$, $R^4$, $R^5$, $R^6$ and X have the abovementioned meanings.

Compounds of the formula IA where Z is $OR^7$ are known from EP-A 386,561 or may be produced by the methods described therein.

The Examples and methods which follow illustrate the preparation of the novel active ingredients and their intermediates.

PREPARATION EXAMPLE 1

N-Methyl-2-[2 '-methyl-4 '-(methoximinoeth-1''-yl)-phenoxymethyl]-phenylglyoxylamide O-methyl oxime a) 225.3 g (1.5 mol) of 4-hydroxy-2-methylacetophenone are dissolved in 600 ml of dry methanol. 150.3 g (1.8 tool) of methoxyamine hydrochloride and 100 g of a molecular sieve are added. Stirring is carried out for 12 hours at room temperature (20° C.). The molecular sieve is filtered off. The filtrate is evaporated down. The remaining residue is taken up in dichloromethane. The organic phase is washed with water, dried and evaporated down. The solid product obtained is washed with pentane and then dried. 252 g (94%) of 4-hydroxy-2-methylacetophenone O-methyl oxime are obtained in the form of a colorless crystalline solid (mp.=96°-98° C.).

b) 89.6 g (0.5 tool) of 4-hydroxy-2-methylacetophenone O-methyl oxime in 300 ml of dry methanol are initially taken under nitrogen. 90 g (0.5 mol) of a 30% strength by weight sodium methylate solution are added dropwise. After 2 hours, the methanol is distilled off. The residue is dissolved in 700 ml of dimethylformamide. 15 g of potassium iodide are added. A solution of 151.6 g (0.53 mol) of methyl 2-(bromomethyl)-phenylglyoxylate O-methyl oxime in 300 ml of methanol are then added dropwise at room temperature under nitrogen. Stirring is carried out for about 10 hours at room temperature, after which the mixture is cooled to about 10° C. and water is added dropwise. The precipitate formed is filtered off, washed with water and pentane and dried. 153.7 g (80%) of methyl 2-[2'-methyl-4'-(methoximinoeth-1''-yl)-phenoxymethyl]-phenylglyoxylate O-methyl oxime are obtained as a colorless crystalline solid (mp.: 138°-140° C.).

c) 4.8 g (0.012 mol) of methyl 2-[2'-methyl-4'-(methoximinoeth-1''-yl)-phenoxymethyl]-phenylglyoxylate O-methyl oxime are dissolved in 32 ml of tetrahydrofuran, and 3.6 g (0.047 mol) of a 40% strength aqueous methylamine solution are added. Thereafter, the reaction mixture is stirred for 6 hours at 40° C. and then evaporated down. The residue was taken up in methyl tert-butyl ether. The organic phase is washed with water, dried and evaporated down again. The remaining crude product is purified by chromatography over a silica gel column (1:1 cyclohexane/ethyl acetate). 3.2 g (67%) of N-methyl-2-[2'-methyl-4'-(methoximinoeth-1''-yl)-phenoxymethyl]phenylglyoxylamide O-methyl oxime are obtained in the form of colorless crystals (mp.: 104°–105° C., compound No. I.007).

PREPARATION EXAMPLE 2

N-Methyl-α-[2-(2'-methyl-4'-(methoximinoeth-1''-yl)-phenoxymethyl)-phenyl]-β-methoxyacrylamide a) Methyl α-(2-bromomethylphenyl)-β-methoxyacrylate and 4-hydroxy-2-methylacetophenone O-methyl oxime are reacted similarly to Method b) (Example 1) to give methyl α-[2-(2'-methyl-4'-(methoximinoeth-1''-yl)-phenoxymethyl)-phenyl]-β-methoxyacrylate. The compound is obtained as a colorless solid (mp.: 118°–120° C.).

b) 3 g (0.0078 mol) of methyl α-[2-(2'-methyl-4'-(methoximinoeth-1''-yl)-phenoxymethyl)-phenyl]-β-methoxyacrylate are dissolved in 15 ml of dry pyridine. 5.2 g (0. 039 mol) of anhydrous lithium iodide are added and stirring is carried out for 8 hours at 130° C. The reaction mixture is evaporated down. The residue is taken up in water. The aqueous phase is first washed with methyl tert-butyl ether and then acidified with hydrochloric acid. The aqueous phase is then extracted with methyl tert-butyl ether. The methyl tert-butyl ether phase is washed with water, dried over sodium sulfate and evaporated down. 2.1 g of α-[2-(2 '-methyl-4'-(methoximinoeth-1''-yl)-phenoxymethyl)-phenyl]-β-methoxyacrylic acid are obtained as a dark resin, which is used for the subsequent reactions without further purification.

c) 2.1 g (0.0056 mol) of α-[2-(2'-methyl-4'-(methoximinoeth-1''-yl) -phenoxymethyl)-phenyl]-β-methoxyacrylic acid and 0.53 g of pyridine in 10 ml of dried diethyl ether are initially taken. 0.8 g (0.0067 mol) of thionyl chloride is added dropwise at 0°–5° C. and stirring is carried out for 10 hours at room temperature. The mixture is filtered. The filtrate is evaporated down. 2 g of α-[2-(2'-methyl-4'-(methoximinoeth-1''-yl)-phenoxymethyl)-phenyl]-β-methoxyacryloyl chloride are obtained as a dark oil, which is used for the subsequent reactions without further purification.

d) 1 g (0.0026 mol) of α-[2-(2'-methyl-4'-(methoximinoeth-1''-yl) -phenoxymethyl)-phenyl]-β-methoxyacryloyl chloride in 10 ml of dichloromethane is initially taken. A solution of 1 g (0.032 mol) of methylamine in 10 ml of dichloromethane is added dropwise at 0°–5° C. Stirring is carried out for 10 hours at room temperature. The reaction mixture is taken up in 20 ml of dichloromethane and the solution is washed with water, dried and evaporated down. The remaining crude product is purified by chromatography over a silica gel column (2:1 n-hexane/acetone). 0.5 g (50%) of N-methyl-α-[2-(2'-methyl-4'-(methoximinoeth-1''-yl)-phenoxymethyl)-phenyl]-β-methoxyacrylamide is obtained in the form of colorless crystals (mp.: 96°–98° C., compound No. I.006).

Compounds I (and IA in which Z is $NR^5R^6$) listed in the Table below may be prepared similarly. Compounds IA where Z is $OR^7$ may be obtained in accordance with the details given in EP-A 386,561. They too are listed in the Table below.

Compounds I (and IA in which Z is $NR^5R^6$) of particular significance with regard to their biological action on pests (plant-pathogenic fungi, and insects, mites and nematodes) are listed in Tables 1, 2, 5–11 and 18–22 which follow.

Further, compounds IA in which Z is $OR^7$ which are of particular significance with regard to their biological action on animal pests (insects, mites and nematodes) are listed in Tables 3, 4, 12–17 and 23–27.

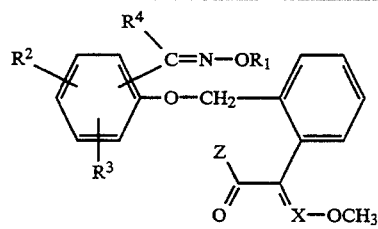

IA

| No. | $R^1$ | $R^2$ | $R^3$ | P* | $R^4$ | Z | X | Phys. data |
|---|---|---|---|---|---|---|---|---|
| I.001 | $CH_3$ | H | H | 3 | $CH_3$ | $NHCH_3$ | N | oil (E; E) $^1$H-NMR (ppm): 2.19(s, 3H); 2.86(d, 3H); 3.93(s, 3H); 3.99(s, 3H); 4.95(s, 2H); 6.7(sbr, 1H), 6.84–7.52(m, 8H) |
| I.002 | $C_2H_5$ | H | H | 3 | $CH_3$ | $NHCH_3$ | N | oil (E; E) $^1$H-NMR (ppm): 1.13(t, 3H); 2.29(s, 3H); 2.85(d, 3H); 3.93(s, 3H); 4.23(q, 2H); 4.96(s, 2H); 6.75(sbr, 1H); 6.86–7.55(m, 8H) |
| I.003 | $CH_2CH=CH_2$ | H | H | 3 | $CH_3$ | $NHCH_3$ | N | oil (E; E) $^1$H-NMR (ppm): 2.2(d, 3H); 2.86(d, 3H); 3.92(s, 3H); 4.69(m, 2H); 4.96(s, 2H); |

-continued

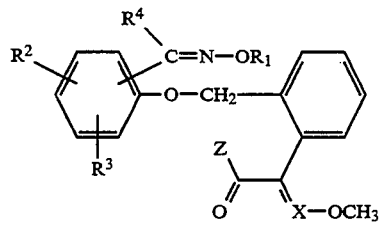

IA

| No. | R¹ | R² | R³ | P* | R⁴ | Z | X | Phys. data |
|---|---|---|---|---|---|---|---|---|
| | | | | | | | | 5.17–5.38(m, 2H); 5.96–6.17(m, 1H); 6.37(sbr, 1H); 6.84–7.54(m, 8H) |
| I.004 | CH(CH₃)₂ | H | H | 3 | CH₃ | NHCH₃ | N | mp: 101–103° C. (E; E) |
| I.005 | CH₃ | 2-Cl | H | 4 | CH₃ | NHCH₃ | N | mp: 123–124° C. (E; E) |
| I.006 | CH₃ | 2-CH₃ | H | 4 | CH₃ | NHCH₃ | CH | mp: 96–98° C. (E; E) |
| I.007 | CH₃ | 2-CH₃ | H | 4 | CH₃ | NHCH₃ | N | mp: 104–105° C. (E; E) |
| I.008 | CH₃ | 2-OCH₃ | H | 4 | CH₃ | NHCH₃ | N | mp: 78–80° C. (E; E) |
| I.009 | CH₃ | 3-CH₃ | H | 4 | CH₃ | NHCH₃ | N | mp: 89–90° C. (E; E) |
| I.010 | C₂H₅ | 2-Cl | H | 4 | CH₃ | NHCH₃ | N | mp: 107–108° C. (E; E) |
| I.011 | C₂H₅ | 2-CH₃ | H | 4 | CH₃ | NHCH₃ | N | mp: 92–94° C. (E; E) |
| I.012 | C₂H₅ | 2-OCH₃ | H | 4 | CH₃ | NHCH₃ | N | mp: 78–81° C. (E; E) |
| I.013 | C₂H₅ | 3-CH₃ | H | 4 | CH₃ | NHCH₃ | N | resin (E; E) |
| I.014 | CH₃ | 2-CH₃ | 5-CH₃ | 4 | CH₃ | NHCH₃ | N | oil (E; E) ¹H-NMR (ppm): 2.13(s, 3H); 2.18(s, 3H); 2.28(s, 3H); 2.87(d, 3H); 3.95("s", 6H); 4.92(s, 2H); 6.61(s, 1H); 6.72(sbr, 1H); 7.00(s, 1H); 7.19–7.56(m, 4H) |
| I.015 | CH₃ | 2-CH₃ | H | 4 | C₂H₅ | NHCH₃ | N | oil (E; E) ¹H-NMR (ppm): 1.1(t, 3H); 2.23(s, 3H); 2.7(q, 2H); 2.86(d, 3H); 3.93(s, 3H); 3.96(s, 3H)4.98(s, 2H); 6.72(sbr, 1H); 6.75–7.55(m, 7H) |
| I.016 | CH₂CH=CH₂ | 2-CH₃ | H | 4 | CH₃ | NHCH₃ | N | mp: 98–106° C. (E; E) |
| I.017 | C₂H₅ | 2-CH₃ | 5-CH₃ | 4 | CH₃ | NHCH₃ | N | resin (E; E) ¹H-NMR (ppm): 1.3(t, 3H); 2.15(s, 3H); 2.17(s, 3H); 2.29(s, 3H); 2.87(d, 3H); 3.95(s, 3H); 4.18(q, 2H); 4.94(s, 2H); 6.61(s, 1H); 6.72(sbr, 1H); 6.99(s, 1H); 7.2–7.57(m, 4H) |
| I.018 | (CH₂)₂CH₃ | 2-CH₃ | H | 4 | CH₃ | NHCH₃ | N | mp: 72–73° C. (E; E) |
| I.019 | (CH₂)₃CH₃ | 2-CH₃ | H | 4 | CH₃ | NHCH₃ | N | mp: 54–56° C. (E; E) |
| I.020 | (CH₂)₅CH₃ | 2-CH₃ | H | 4 | CH₃ | NHCH₃ | N | mp: 96–98° C. (E; E) |
| I.021 | CH₂CH=CH₂ | 2-CH₃ | 5-CH₃ | 4 | CH₃ | NHCH₃ | N | mp: 61–63° C. (E; E) |
| I.022 | (CH₂)₃CH₃ | 2-CH₃ | 5-CH₃ | 4 | CH₃ | NHCH₃ | N | mp: 49–52° C. (E; E) |
| I.023 | CH₂CH=CH₂ | 2-CH₃ | H | 4 | C₂H₅ | NHCH₃ | N | mp: 71–73° C. (E; E) |
| I.024 | CH₃ | 2-CH₃ | H | 4 | CH(CH₃)₂ | NHCH₃ | N | resin (E; E) |
| I.025 | C₂H₅ | 2-CH₃ | H | 4 | C₂H₅ | NHCH₃ | N | mp: 94–96° C. (E; E) |
| I.026 | (CH₂)₂CH₃ | 2-CH₃ | 5-CH₃ | 4 | CH₃ | NHCH₃ | N | mp: 76–79° C. (E; E) |
| I.027 | (CH₂)₂CH₃ | 2-CH₃ | H | 4 | C₂H₅ | NHCH₃ | N | mp: 86–88° C. (E; E) |
| I.028 | (CH₂)₂OCH₃ | 2-CH₃ | H | 4 | CH₃ | NHCH₃ | N | resin (E; E) |
| I.029 | (CH₂)₂OCH₃ | 2-CH₃ | H | 4 | C₂H₅ | NHCH₃ | N | resin (E; E) |
| I.030 | (CH₂)₃CH₃ | 2-CH₃ | H | 4 | C₂H₅ | NHCH₃ | N | mp: 74–76° C. (E; E) |
| I.031 | (CH₂)₂OCH₃ | 2-CH₃ | 5-CH₃ | 4 | CH₃ | NHCH₃ | N | mp: 87–89° C. (E; E) |
| I.032 | CH₃ | 2-CH₃ | 5-CH₃ | 4 | C₂H₅ | NHCH₃ | N | resin (E; E) |
| I.033 | C₂H₅ | 2-CH₃ | 5-CH₃ | 4 | C₂H₅ | NHCH₃ | N | resin (E; E) |
| I.034 | (CH₂)₂CH₃ | 2-CH₃ | 5-CH₃ | 4 | C₂H₅ | NHCH₃ | N | mp: 58–66° C. (E; E) |
| I.035 | CH₂CH=CH₂ | 2-CH₃ | 5-CH₃ | 4 | C₂H₅ | NHCH₃ | N | resin (E; E) |
| I.036 | (CH₂)₂OCH₃ | 2-CH₃ | 5-CH₃ | 4 | C₂H₅ | NHCH₃ | N | resin (E; E) |
| I.037 | (CH₂)₃CH₃ | 2-CH₃ | 5-CH₃ | 4 | C₂H₅ | NHCH₃ | N | mp: 58–60° C. (E; E) |
| I.038 | (CH₂)₂CH₃ | 2-Cl | H | 4 | CH₃ | NHCH₃ | N | mp: 84–86° C. (E; E) |
| I.039 | (CH₂)₃CH₃ | 2-Cl | H | 4 | CH₃ | NHCH₃ | N | mp: 92–94° C. (E; E) |
| I.040 | CH₂CH=CH₂ | 2-Cl | H | 4 | CH₃ | NHCH₃ | N | mp: 80–82° C. (E; E) |
| I.041 | CH₃ | 2-CH₃ | H | 4 | (CH₂)₂CH₃ | NHCH₃ | N | mp: 105–107° C. (E; E) |
| I.042 | (CH₂)₅CH₃ | 2-CH₃ | 5-CH₃ | 4 | CH₃ | NHCH₃ | N | mp: 52–54° C. (E; E) |
| I.043 | CH₂C≡CH | 2-CH₃ | H | 4 | CH₃ | NHCH₃ | N | mp: 142–144° C. (E; E) |
| I.044 | CH₂C≡CH | 2-CH₃ | H | 4 | C₂H₅ | NHCH₃ | N | mp: 88–90° C. (E; E) |
| I.045 | CH₂C≡CH | 2-CH₃ | 5-CH₃ | 4 | CH₃ | NHCH₃ | N | mp: 99–101° C. (E; E) |
| I.046 | CH₂CH=CHCl | 2-CH₃ | H | 4 | CH₃ | NHCH₃ | N | mp: 67–69° C. (E; E) |
| I.047 | CH₂CH=CHCl | 2-CH₃ | H | 4 | C₂H₅ | NHCH₃ | N | mp: 108–110° C. (E; E) |
| I.048 | CH₂CH=CHCl | 2-CH₃ | 5-CH₃ | 4 | CH₃ | NHCH₃ | N | mp: 110–112° C. (E; E) |
| I.049 | CH₂CN | 2-CH₃ | H | 4 | CH₃ | NHCH₃ | N | mp: 114–116° C. (E; E) |

-continued

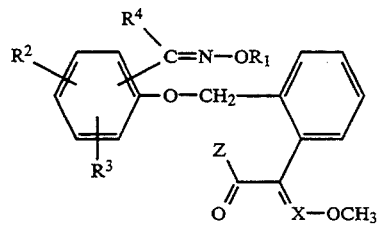

IA

| No. | R¹ | R² | R³ | P* | R⁴ | Z | X | Phys. data |
|---|---|---|---|---|---|---|---|---|
| I.050 | CH₂CN | 2-CH₃ | 5-CH₃ | 4 | CH₃ | NHCH₃ | N | mp: 104–106° C. (E; E) |
| I.051 | CH₃ | 2-CH₃ | H | 4 | C₆H₅ | NHCH₃ | N | resin (E; E) |
| I.052 | (CH₂)₂CH₃ | 2-CH₃ | H | 4 | C₆H₅ | NHCH₃ | N | resin (E; E) |
| I.053 | CH₃ | H | H | 2 | H | OCH₃ | CH | mp: 82–84° C. (E; E) |
| I.054 | CH₃ | H | H | 2 | H | OCH₃ | N | mp: 73–76° C. (E; E) |
| I.055 | C₂H₅ | H | H | 2 | H | OCH₃ | CH | mp: 86–88° C. (E; E) |
| I.056 | C₂H₅ | H | H | 2 | H | OCH₃ | N | mp: 89–90° C. (E; E) |
| I.057 | C₂H₅ | 4-Cl | H | 2 | H | OCH₃ | CH | mp: 95–97° C. (E; E) |
| I.058 | CH₃ | H | H | 3 | H | OCH₃ | CH | mp: 75–77° C. (E; E) |
| I.059 | CH₃ | H | H | 3 | H | OCH₃ | N | oil (E; E) |
| I.060 | C₂H₅ | H | H | 3 | H | OCH₃ | CH | oil (E; E)<br>¹H-NMR (ppm): 1.28(t, 3H); 3.69(s, 3H); 3.73(s, 3H); 4.20(q, 2H); 4.97(s, 2H); 6.85–7.53(m, 8H); 7.57(s, 1H); 8,0(s, 1H) |
| I.061 | C₂H₅ | H | H | 3 | H | OCH₃ | N | oil (E; E) |
| I.062 | C₂H₅ | 6-OCH₃ | H | 3 | H | OCH₃ | CH | mp: 96–98° C. (E; E) |
| I.063 | C₂H₅ | 6-OCH₃ | H | 3 | H | OCH₃ | N | mp: 124–126° C. (E; E) |
| I.064 | CH₂CH=CH₂ | H | H | 3 | H | OCH₃ | CH | oil (E; E) |
| I.065 | CH₂CH=CH₂ | H | H | 3 | H | OCH₃ | N | oil (E; E) |
| I.066 | CH(CH₃)₂ | H | H | 3 | H | OCH₃ | CH | oil (E; E) |
| I.067 | CH(CH₃)₂ | H | H | 3 | H | OCH₃ | N | oil (E; E) |
| I.068 | (CH₂)₃CH₃ | H | H | 3 | H | OCH₃ | CH | oil (E; E) |
| I.069 | (CH₂)₃CH₃ | H | H | 3 | H | OCH₃ | N | oil (E; E) |
| I.070 | (CH₂)₅CH₃ | H | H | 3 | H | OCH₃ | CH | oil (E; E) |
| I.071 | (CH₂)₅CH₃ | H | H | 3 | H | OCH₃ | N | oil (E; E) |
| I.072 | CH₂C₆H₅ | H | H | 3 | H | OCH₃ | CH | oil (E; E) |
| I.073 | CH₂C₆H₅ | H | H | 3 | H | OCH₃ | N | oil (E; E) |
| I.074 | C₂H₅ | 6-OC₂H₅ | H | 3 | H | OCH₃ | CH | mp: 83–85° C. (E; E) |
| I.075 | C₂H₅ | 6-OC₂H₅ | H | 3 | H | OCH₃ | N | mp: 104–106° C. (E; E) |
| I.076 | (CH₂)₄CH₃ | H | H | 3 | H | OCH₃ | N | oil (E; E) |
| I.077 | CH₂-(2-F—C₆H₄) | H | H | 3 | H | OCH₃ | CH | oil (E; E) |
| I.078 | CH₂-(2-F—C₆H₄) | H | H | 3 | H | OCH₃ | N | oil (E; E) |
| I.079 | CH₂-(3-F—C₆H₄) | H | H | 3 | H | OCH₃ | CH | oil (E; E) |
| I.080 | CH₂-(3-F—C₆H₄) | H | H | 3 | H | OCH₃ | N | oil (E; E) |
| I.081 | CH₂-(2-Cl—C₆H₄) | H | H | 3 | H | OCH₃ | CH | oil (E; E) |
| I.082 | (3,4-Cl₂—C₆H₃)—<br>—CH₂ | H | H | 3 | H | OCH₃ | CH | oil (E; E) |
| I.083 | (3,4-Cl₂—C₆H₃)—<br>—CH₂ | H | H | 3 | H | OCH₃ | N | oil (E; E) |
| I.084 | (2,6-Cl₂—C₆H₃)—<br>—CH₂ | H | H | 3 | H | OCH₃ | CH | oil (E; E) |
| I.085 | (2,6-Cl₂—C₆H₃)—<br>—CH₂ | H | H | 3 | H | OCH₃ | N | oil (E; E) |
| I.086 | (CH₂)₂C₆H₅ | H | H | 3 | H | OCH₃ | CH | oil (E; E) |
| I.087 | (CH₂)₂C₆H₅ | H | H | 3 | H | OCH₃ | N | oil (E; E) |
| I.088 | (CH₂)₂CH=CHC₆H₅ | H | H | 3 | H | OCH₃ | CH | oil (E; E) |
| I.089 | (CH₂)₂CH=CHC₆H₅ | H | H | 3 | H | OCH₃ | N | oil (E; E) |
| I.090 | (4-Cl—C₆H₄)—<br>—CH₂CH=CHCH₂ | H | H | 3 | H | OCH₃ | CH | oil (E; E) |
| I.091 | (4-Cl—C₆H₄)—<br>—CH₂CH=CHCH₂ | H | H | 3 | H | OCH₃ | N | oil (E; E) |
| I.092 | (4-CF₃—C₆H₄)—<br>—CH₂CH=CHCH₂ | H | H | 3 | H | OCH₃ | CH | oil (E; E) |
| I.093 | (4-CF₃—C₆H₄)—<br>—CH₂CH=CHCH₂ | H | H | 3 | H | OCH₃ | N | oil (E; E) |
| I.094 | CH₃ | H | H | 3 | CH₃ | OCH₃ | CH | oil (E; E) |
| I.095 | CH₃ | H | H | 3 | CH₃ | OCH₃ | N | oil (E; E) |
| I.096 | C₂H₅ | H | H | 3 | CH₃ | OCH₃ | CH | oil (E; E)<br>¹H-NMR (ppm): 1.32(t, 3H); 2.18(s, 3H); 3.68(s, 3H); 3.77(s, 3H); 4.22(q, 2H); 4.97(s, 2H); 6.83–7.53(m, 8H); 7.55(s, 1H) |
| I.097 | C₂H₅ | H | H | 3 | CH₃ | OCH₃ | N | oil (E; E)<br>¹H-NMR (ppm): 1.32(t, 3H); 2.17(s, 3H); 3.82(s, 3H); |

-continued

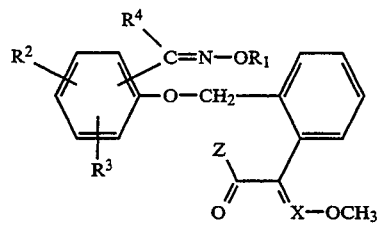

IA

| No. | R¹ | R² | R³ | P* | R⁴ | Z | X | Phys. data |
|---|---|---|---|---|---|---|---|---|
| | | | | | | | | 4.0(s, 3H); 4.23(q, 4H); 4.97(s, 2H); 6.83–7.57(m, 8H) |
| I.098 | (CH₂)₂CH₃ | H | H | 3 | CH₃ | OCH₃ | CH | oil (E; E) |
| I.099 | (CH₂)₂CH₃ | H | H | 3 | CH₃ | OCH₃ | N | mp: 73–74° C. (E; E) |
| I.100 | CH₂CH=CH₂ | H | H | 3 | CH₃ | OCH₃ | CH | oil (E; E) |
| I.101 | CH₂CH=CH₂ | H | H | 3 | CH₃ | OCH₃ | N | mp: 51–53° C. (E; E) |
| I.102 | CH(CH₃)₂ | H | H | 3 | CH₃ | OCH₃ | CH | oil (E; E) |
| I.103 | CH(CH₃)₂ | H | H | 3 | CH₃ | OCH₃ | N | mp: 58–60° C. (E; E) |
| I.104 | (CH₂)₃CH₃ | H | H | 3 | CH₃ | OCH₃ | CH | oil (E; E) |
| I.105 | (CH₂)₃CH₃ | H | H | 3 | CH₃ | OCH₃ | N | oil (E; E) ¹H-NMR (ppm): 0.95(t, 3H); 1.43(m, 2H); 1.7(m, 2H); 2.18(s, 3H); 3.83(s, 3H); 4.0(s, 3H); 4.17(t, 2H); 4.97(s, 2H); 6.82–7.55(m, 8H) |
| I.106 | CH₂CH=CHCH₃ | H | H | 3 | CH₃ | OCH₃ | CH | oil (E; E) |
| I.107 | CH₂CH=CHCH₃ | H | H | 3 | CH₃ | OCH₃ | N | mp: 76–78° C. (E; E) |
| I.108 | (CH₂)₅CH₃ | H | H | 3 | CH₃ | OCH₃ | CH | oil (E; E) |
| I.109 | (CH₂)₅CH₃ | H | H | 3 | CH₃ | OCH₃ | N | oil (E; E) ¹H-NMR (ppm): 0.87(t, 3H); 1.32(m, 6H); 1.7(m, 2H); 2.18(s, 3H); 3.83(s, 3H); 4.02(s, 3H); 4.17(t, 2H); 4.95(s, 2H); 6.83–7.57(m, 8H) |
| I.110 | CH₂C₆H₅ | H | H | 3 | CH₃ | OCH₃ | N | oil (E; E) ¹H-NMR (ppm): 2.22(s, 3H); 3.78(s, 3H); 4.0(s, 3H); 4.97(s, 2H); 5.23(s, 2H); 6.82–7.53(m, 8H) |
| I.111 | CH₂CH=CHCl | H | H | 3 | CH₃ | OCH₃ | CH | oil (E; E) |
| I.112 | CH₂CH=CHCl | H | H | 3 | CH₃ | OCH₃ | N | oil (E; E) |
| I.113 | C(CH₃)₂CH₃ | H | H | 3 | CH₃ | OCH₃ | CH | oil (E; E) |
| I.114 | C(CH₃)₂CH₃ | H | H | 3 | CH₃ | OCH₃ | N | mp: 83–85° C. (E; E) |
| I.115 | CH₂CH(CH₃)₂ | H | H | 3 | CH₃ | OCH₃ | CH | oil (E; E) |
| I.116 | CH₂CH(CH₃)₂ | H | H | 3 | CH₃ | OCH₃ | N | mp: 70–72° C. (E; E) |
| I.117 | CH₂C(CH₃)=CH₂ | H | H | 3 | CH₃ | OCH₃ | CH | oil (E; E) |
| I.118 | CH₂C(CH₃)=CH₂ | H | H | 3 | CH₃ | OCH₃ | N | mp: 64–65° C. (E; E) |
| I.119 | (CH₂)₂CH(CH₃)₂ | H | H | 3 | CH₃ | OCH₃ | CH | oil (E; E) |
| I.120 | (CH₂)₂CH(CH₃)₂ | H | H | 3 | CH₃ | OCH₃ | N | oil (E; E) |
| I.121 | CH₃ | H | H | 4 | H | OCH₃ | CH | mp: 84–86° C. (E; E) |
| I.122 | CH₃ | H | H | 4 | H | OCH₃ | N | mp: 88–91° C. (E; E) |
| I.123 | CH₃ | 2-OCH₃ | H | 4 | H | OCH₃ | CH | oil (E; E) |
| I.124 | CH₃ | 2-OCH₃ | H | 4 | H | OCH₃ | N | mp: 105–107° C. (E; E) |
| I.125 | C₂H₅ | H | H | 4 | H | OCH₃ | CH | mp: 108–110° C. (E; E) |
| I.126 | C₂H₅ | H | H | 4 | H | OCH₃ | N | mp: 106–108° C. (E; E) |
| I.127 | CH₂CH=CH₂ | H | H | 4 | H | OCH₃ | CH | mp: 103–105° C. (E; E) |
| I.128 | CH₂CH=CH₂ | H | H | 4 | H | OCH₃ | N | mp: 82–84° C. (E; E) |
| I.129 | (CH₂)₅CH₃ | H | H | 4 | H | OCH₃ | CH | mp: 62–63° C. (E; E) |
| I.130 | (CH₂)₅CH₃ | H | H | 4 | H | OCH₃ | N | mp: 72–73° C. (E; E) |
| I.131 | CH₂C₆H₅ | H | H | 4 | H | OCH₃ | N | mp: 103–105° C. (E; E) |
| I.132 | CH₂-(4-Cl—C₆H₄) | H | H | 4 | H | OCH₃ | CH | mp: 151–153° C. (E; E) |
| I.133 | CH₂CH=CHCl | H | H | 4 | H | OCH₃ | CH | oil (E; E) |
| I.134 | CH₂CH=CHCl | H | H | 4 | H | OCH₃ | N | mp: 95–97° C. (E; E) |
| I.135 | CH₂C(CH₃)=CH₂ | H | H | 4 | H | OCH₃ | CH | mp: 100–102° C. (E; E) |
| I.136 | CH₂C(CH₃)=CH₂ | H | H | 4 | H | OCH₃ | N | mp: 95–96° C. (E; E) |
| I.137 | (CH₂)₄CH₃ | H | H | 4 | H | OCH₃ | N | oil (E; E) |
| I.138 | CH₃ | H | H | 4 | CH₃ | OCH₃ | CH | oil (E; E) |
| I.139 | CH₃ | H | H | 4 | CH₃ | OCH₃ | N | mp: 99–100° C. (E; E) |
| I.140 | CH₃ | 2-Cl | H | 4 | CH₃ | OCH₃ | N | mp: 93–94° C. (E; E) |
| I.141 | CH₃ | 2-CH₃ | H | 4 | CH₃ | OCH₃ | N | mp: 137–139° C. (E; E) |
| I.142 | CH₃ | 2-OCH₃ | H | 4 | CH₃ | OCH₃ | N | mp: 82–84° C. (E; E) |
| I.143 | CH₃ | 3-CH₃ | H | 4 | CH₃ | OCH₃ | N | mp: 55–56° C. (E; E) |
| I.144 | C₂H₅ | H | H | 4 | CH₃ | OCH₃ | CH | mp: 71–73° C. (E; E) |
| I.145 | C₂H₅ | H | H | 4 | CH₃ | OCH₃ | N | mp: 79–80° C. (E; E) |
| I.146 | C₂H₅ | 2-Cl | H | 4 | CH₃ | OCH₃ | N | mp: 88–90° C. (E; E) |
| I.147 | C₂H₅ | 2-CH₃ | H | 4 | CH₃ | OCH₃ | N | mp: 109–111° C. (E; E) |

-continued

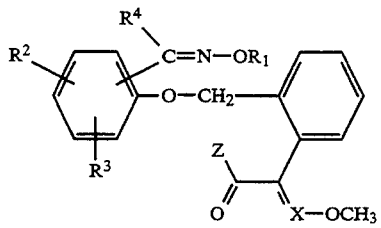

IA

| No. | R¹ | R² | R³ | P* | R⁴ | Z | X | Phys. data |
|---|---|---|---|---|---|---|---|---|
| I.148 | C₂H₅ | 2-OCH₃ | H | 4 | CH₃ | OCH₃ | N | mp: 96–98° C. (E; E) |
| I.149 | C₂H₅ | 3-CH₃ | H | 4 | CH₃ | OCH₃ | N | resin (E; E) |
| I.150 | (CH₂)₂CH₃ | H | H | 4 | CH₃ | OCH₃ | CH | mp: 87–99° C. (E; E) |
| I.151 | (CH₂)₂CH₃ | H | H | 4 | CH₃ | OCH₃ | N | mp: 100–101° C. (E; E) |
| I.152 | CH₂CH=CH₂ | H | H | 4 | CH₃ | OCH₃ | CH | mp: 90–92° C. (E; E) |
| I.153 | CH₂CH=CH₂ | H | H | 4 | CH₃ | OCH₃ | N | mp: 107–108° C. (E; E) |
| I.154 | CH(CH₃)₂ | H | H | 4 | CH₃ | OCH₃ | CH | mp: 120–123° C. (E; E) |
| I.155 | CH(CH₃)₂ | H | H | 4 | CH₃ | OCH₃ | N | mp: 109–110° C. (E; E) |
| I.156 | (CH₂)₃CH₃ | H | H | 4 | CH₃ | OCH₃ | CH | mp: 64–66° C. (E; E) |
| I.157 | (CH₂)₃CH₃ | H | H | 4 | CH₃ | OCH₃ | N | oil (E; E) $^1$H-NMR (ppm): 0.97(t, 3H); 1.4(m, 2H); 1.68(m, 2H); 2.17(s, 3H); 3.83(s, 3H); 4.0(s, 3H); 4.15(t, 2H); 4.95(s, 2H); 6.82–7.57(m, 8H) |
| I.158 | CH₂CH=CHCH₃ | H | H | 4 | CH₃ | OCH₃ | CH | oil (E; E) |
| I.159 | CH₂CH=CHCH₃ | H | H | 4 | CH₃ | OCH₃ | N | mp: 100–103° C. (E; E) |
| I.160 | (CH₂)₅CH₃ | H | H | 4 | CH₃ | OCH₃ | CH | mp: 65–67° C. (E; E) |
| I.161 | (CH₂)₅CH₃ | H | H | 4 | CH₃ | OCH₃ | N | mp: 60–63° C. (E; E) |
| I.162 | CH₂C₆H₅ | H | H | 4 | CH₃ | OCH₃ | CH | mp: 110–112° C. (E; E) |
| I.163 | CH₂C₆H₅ | H | H | 4 | CH₃ | OCH₃ | N | mp: 104–106° C. (E; E) |
| I.164 | CH₂CH=CHCl | H | H | 4 | CH₃ | OCH₃ | CH | mp: 98–100° C. (E; E) |
| I.165 | CH₂CH=CHCl | H | H | 4 | CH₃ | OCH₃ | N | mp: 105–107° C. (E; E) |
| I.166 | C(CH₃)₃ | H | H | 4 | CH₃ | OCH₃ | CH | mp: 88–90° C. (E; E) |
| I.167 | C(CH₃)₃ | H | H | 4 | CH₃ | OCH₃ | N | mp: 75–78° C. (E; E) |
| I.168 | CH₂CH(CH₃)₂ | H | H | 4 | CH₃ | OCH₃ | CH | mp: 85–87° C. (E; E) |
| I.169 | CH₂CH(CH₃)₂ | H | H | 4 | CH₃ | OCH₃ | N | mp: 79–81° C. (E; E) |
| I.170 | CH₂C(CH₃)=CH₂ | H | H | 4 | CH₃ | OCH₃ | CH | mp: 94–96° C. (E; E) |
| I.171 | CH₂C(CH₃)=CH₂ | H | H | 4 | CH₃ | OCH₃ | N | mp: 88–89° C. (E; E) |
| I.172 | (CH₂)₂CH(CH₃)₂ | H | H | 4 | CH₃ | OCH₃ | CH | mp: 46–48° C. (E; E) |
| I.173 | (CH₂)₂CH(CH₃)₂ | H | H | 4 | CH₃ | OCH₃ | N | oil (E; E) |
| I.174 | CH₃ | 2-CH₃ | 5-CH₃ | 4 | CH₃ | OCH₃ | N | mp: 104–107° C. (E; E) |
| I.175 | CH₃ | 2-CH₃ | H | 4 | C₂H₅ | OCH₃ | N | mp: 84–87° C. (E; E) |
| I.176 | CH₂CH=CH₂ | 2-CH₃ | H | 4 | CH₃ | OCH₃ | N | mp: 78–80° C. (E; E) |
| I.177 | C₂H₅ | 2-CH₃ | 5-CH₃ | 4 | CH₃ | OCH₃ | N | mp: 79–81° C. (E; E) |
| I.178 | (CH₂)₂CH₃ | 2-CH₃ | H | 4 | CH₃ | OCH₃ | N | mp: 88–89° C. (E; E) |
| I.179 | (CH₂)₃CH₃ | 2-CH₃ | H | 4 | CH₃ | OCH₃ | N | mp: 77–79° C. (E; E) |
| I.180 | CH₂CH=CH₂ | 2-CH₃ | 5-CH₃ | 4 | CH₃ | OCH₃ | N | mp: 65–68° C. (E; E) |
| I.181 | (CH₂)₃CH₃ | 2-CH₃ | 5-CH₃ | 4 | CH₃ | OCH₃ | N | mp: 58–62° C. (E; E) |
| I.182 | CH₂CH=CH₂ | 2-CH₃ | H | 4 | C₂H₅ | OCH₃ | N | mp: 69–71° C. (E; E) |
| I.183 | C₂H₅ | 2-CH₃ | H | 4 | C₂H₅ | OCH₃ | N | mp: 73–75° C. (E; E) |
| I.184 | (CH₂)₂CH₃ | 2-CH₃ | 5-CH₃ | 4 | CH₃ | OCH₃ | N | mp: 44–45° C. (E; E) |
| I.185 | (CH₂)₂CH₃ | 2-CH₃ | H | 4 | C₂H₅ | OCH₃ | N | mp: 90–92° C. (E; E) |
| I.186 | (CH₂)₂OCH₃ | 2-CH₃ | H | 4 | CH₃ | OCH₃ | N | mp: 85–87° C. (E; E) |
| I.187 | (CH₂)₂OCH₃ | 2-CH₃ | H | 4 | C₂H₅ | OCH₃ | N | mp: 65–68° C. (E; E) |
| I.188 | (CH₂)₃CH₃ | 2-CH₃ | H | 4 | C₂H₅ | OCH₃ | N | mp: 92–93° C. (E; E) |
| I.189 | (CH₂)₂OCH₃ | 2-CH₃ | 5-CH₃ | 4 | CH₃ | OCH₃ | N | mp: 82–84° C. (E; E) |
| I.190 | CH₃ | 2-CH₃ | 5-CH₃ | 4 | C₂H₅ | OCH₃ | N | mp: 109–111° C. (E; E) |
| I.191 | C₂H₅ | 2-CH₃ | 5-CH₃ | 4 | C₂H₅ | OCH₃ | N | mp: 87–89° C. (E; E) |
| I.192 | (CH₂)₂CH₃ | 2-CH₃ | 5-CH₃ | 4 | C₂H₅ | OCH₃ | N | mp: 99–100° C. (E; E) |
| I.193 | CH₂CH=CH₂ | 2-CH₃ | 5-CH₃ | 4 | C₂H₅ | OCH₃ | N | mp: 83–85° C. (E; E) |
| I.194 | (CH₂)₂OCH₃ | 2-CH₃ | 5-CH₃ | 4 | C₂H₅ | OCH₃ | N | mp: 81–83° C. (E; E) |
| I.195 | (CH₂)₃CH₃ | 2-CH₃ | 5-CH₃ | 4 | C₂H₅ | OCH₃ | N | mp: 81–83° C. (E; E) |
| I.196 | (CH₂)₂CH₃ | 2-Cl | H | 4 | CH₃ | OCH₃ | N | mp: 67–70° C. (E; E) |
| I.197 | (CH₂)₃CH₃ | 2-Cl | H | 4 | CH₃ | OCH₃ | N | mp: 66–68° C. (E; E) |
| I.198 | CH₂CH=CH₂ | 2-Cl | H | 4 | CH₃ | OCH₃ | N | mp: 91–92° C. (E; E) |
| I.199 | CH₂CH≡CH | 2-CH₃ | H | 4 | CH₃ | OCH₃ | N | mp: 107–109° C. (E; E) |
| I.200 | CH₂CH≡CH | 2-CH₃ | H | 4 | C₂H₅ | OCH₃ | N | mp: 100–102° C. (E; E) |
| I.201 | CH₂CH≡CH | 2-CH₃ | 5-CH₃ | 4 | CH₃ | OCH₃ | N | mp: 87–89° C. (E; E) |
| I.202 | CH₂CH=CHCl | 2-CH₃ | H | 4 | CH₃ | OCH₃ | N | mp: 118–120° C. (E; E) |
| I.203 | CH₂CH=CHCl | 2-CH₃ | H | 4 | C₂H₅ | OCH₃ | N | mp: 95–97° C. (E; E) |
| I.204 | CH₂CH=CHCl | 2-CH₃ | 5-CH₃ | 4 | CH₃ | OCH₃ | N | mp: 89–91° C. (E; E) |
| I.205 | CH₃ | 2-CH₃ | H | 4 | C₆H₅ | OCH₃ | N | resin (E; E) |
| I.206 | (CH₂)₂CH₃ | 2-CH₃ | H | 4 | C₆H₅ | OCH₃ | N | resin (E; E) |
| I.207 | CH₂CO₂C(CH₃)₃ | 2-CH₃ | H | 4 | CH₃ | OCH₃ | N | resin (E; E) |
| I.208 | (CH₂)₃—CO₂C(CH₃)₃ | 2-CH₃ | H | 4 | CH₃ | OCH₃ | N | mp: 67–69° C. (E; E) |
| I.209 | (CH₂)₄— | 2-CH₃ | H | 4 | CH₃ | OCH₃ | N | mp: 54–56° C. (E; E) |

-continued

IA

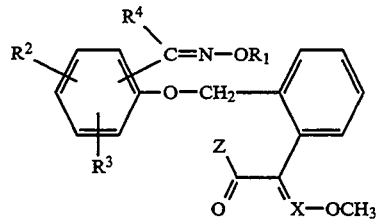

| No. | R¹ | R² | R³ | P* | R⁴ | Z | X | Phys. data |
|---|---|---|---|---|---|---|---|---|
| I.210 | (CH₂)₄—CO₂C(CH₃)₃ | 2-CH₃ | H | 4 | CH₃ | OCH₃ | CH | resin (E; E) |
| I.211 | (CH₂)₅—CO₂C(CH₃)₃ | 2-CH₃ | H | 4 | CH₃ | OCH₃ | N | mp: 46–48° C. (E; E) |
| I.212 | (CH₂)₅—CO₂C(CH₃)₃ | 2-CH₃ | H | 4 | CH₃ | OCH₃ | CH | mp: 56–58° C. (E; E) |
| I.213 | CH₂CH≡CH | 2-CH₃ | 5-CH₃ | 4 | C₂H₅ | OCH₃ | N | resin (E; E) |
| I.214 | CH₃ | 2-CH₃ | H | 4 | CH₃ | N(CH₃)₂ | N | mp: 78–80° C. (E; E) |
| I.215 | CH₃ | 2-CH₃ | H | 4 | CH₃ | N(CH₃)₂ | CH | resin (E; E) |
| I.216 | C₂H₅ | 2-CH₃ | H | 4 | CH₃ | N(CH₃)₂ | N | resin (E; E) |
| I.217 | CH₃ | 2-CH₃ | H | 4 | CH₃ | NH₂ | CH | mp: 143–144° C. (E; E) |
| I.218 | CH₃ | 2-CH₃ | H | 4 | CH₃ | NHC₂H₅ | CH | mp: 110–111° C. (E; E) |
| I.219 | CH₃ | 2-CH₃ | H | 4 | CH₃ | N(CH₃)C₂H₅ | CH | resin (E; E) |
| I.220 | CH₃ | 2-CH₃ | H | 4 | c-C₃H₅ | NHCH₃ | N | ¹H-NMR (ppm): 0.6–2.79(m, 5H); 2.2(s, 3H); 2.9(d, 3H); 3.9(s, 3H); 3.95(s, 3H); 4.97(s, 2H); 6.7–7.6(m, 6H) |
| I.221 | C₂H₅ | 2-CH₃ | H | 4 | c-C₃H₅ | NHCH₃ | N | ¹H-NMR (ppm): 0.6–1.8(m, 8H); 2.2(s, 3H); 2.88(d, 3H); 3.95(s, 3H); 4.2(q, 2H); 4.93(s, 2H); 6.7–7.6(m, 8H) |
| I.222 | (CH₂)₂CH₃ | 2-CH₃ | H | 4 | c-C₃H₅ | NHCH₃ | N | ¹H-NMR (ppm): 0.6–1.78(m, 10H); 2.2(s, 3H); 2.9(d, 3H); 3.92(s, 3H); 4.1(t, 2H); 4.97(s, 2H); 6.62–7.9(m, 8H) |
| I.223 | CH₃ | 2-Cl | 5-CH₃ | 4 | CH₃ | NHCH₃ | N | mp: 80–83° C. (E; E) |
| I.224 | C₂H₅ | 2-Cl | 5-CH₃ | 4 | CH₃ | NHCH₃ | N | mp: 96–98° C. (E; E) |
| I.225 | CH₃ | 2-Cl | 5-Cl | 4 | CH₃ | NHCH₃ | N | mp: 121–122° C. (E; E) |
| I.226 | C₂H₅ | 2-Cl | 5-Cl | 4 | CH₃ | NHCH₃ | N | mp: 105–107° C. (E; E) |
| I.227 | CH₃ | 2-F | H | 4 | CH₃ | NHCH₃ | N | mp: 80–81° C. (E; E) |
| I.228 | C₂H₅ | 2-F | H | 4 | CH₃ | NHCH₃ | N | mp: 63–64° C. (E; E) |
| I.229 | (CH₂)₂CH₃ | 2-F | H | 4 | CH₃ | NHCH₃ | N | mp: 86–87° C. (E; E) |
| I.230 | (CH₂)₃CH₃ | 2-F | H | 4 | CH₃ | NHCH₃ | N | mp: 49–51° C. (E; E) |
| I.231 | CH₂CH=CH₂ | 2-F | H | 4 | CH₃ | NHCH₃ | N | mp: 82–83° C. (E; E) |
| I.232 | CH₃ | 2-Br | H | 4 | CH₃ | NHCH₃ | N | mp: 136–138° C. (E; E) |
| I.233 | C₂H₅ | 2-Br | H | 4 | CH₃ | NHCH₃ | N | mp: 115–117° C. (E; E) |
| I.234 | (CH₂)₂CH₃ | 2-Br | H | 4 | CH₃ | NHCH₃ | N | mp: 95–96° C. (E; E) |
| I.235 | (CH₂)₃CH₃ | 2-Br | H | 4 | CH₃ | NHCH₃ | N | mp: 102–103° C. (E; E) |
| I.236 | CH₂CH=CH₂ | 2-Br | H | 4 | CH₃ | NHCH₃ | N | mp: 119–120° C. (E; E) |
| I.237 | CH₃ | 2-C₂H₅ | H | 4 | CH₃ | NHCH₃ | N | mp: 89–91° C. (E; E) |
| I.238 | C₂H₅ | 2-C₂H₅ | H | 4 | CH₃ | NHCH₃ | N | mp: 83–84° C. (E; E) |
| I.239 | (CH₂)₂CH₃ | 2-C₂H₅ | H | 4 | CH₃ | NHCH₃ | N | mp: 87–88° C. (E; E) |
| I.240 | (CH₂)₃CH₃ | 2-C₂H₅ | H | 4 | CH₃ | NHCH₃ | N | mp: 84–85° C. (E; E) |
| I.241 | CH₂CH=CH₂ | 2-C₂H₅ | H | 4 | CH₃ | NHCH₃ | N | mp: 82–83° C. (E; E) |
| I.242 | (CH₂)₂CH₃ | 2-Cl | 5-Cl | 4 | CH₃ | NHCH₃ | N | mp: 89–91° C. (E; E) |
| I.243 | (CH₂)₂CH₃ | 2-Cl | 5-CH₃ | 4 | CH₃ | NHCH₃ | N | mp: 85–86° C. (E; E) |
| I.244 | CH₃ | 2-Cl | 5-CH₃ | 4 | CH₃ | OCH₃ | N | resin (E; E) |
| I.245 | C₂H₅ | 2-Cl | 5-CH₃ | 4 | CH₃ | OCH₃ | N | mp: 65–67° C. (E; E) |
| I.246 | CH₃ | 2-Cl | 5-Cl | 4 | CH₃ | OCH₃ | N | mp: 73–74° C. (E; E) |
| I.247 | C₂H₅ | 2-Cl | 5-Cl | 4 | CH₃ | OCH₃ | N | mp: 79–80° C. (E; E) |
| I.248 | CH₃ | 2-F | H | 4 | CH₃ | OCH₃ | N | mp: 88–89° C. (E; E) |
| I.249 | C₂H₅ | 2-F | H | 4 | CH₃ | OCH₃ | N | mp: 65–66° C. (E; E) |
| I.250 | (CH₂)₂CH₃ | 2-F | H | 4 | CH₃ | OCH₃ | N | mp: 103–104° C. (E; E) |
| I.251 | (CH₂)₃CH₃ | 2-F | H | 4 | CH₃ | OCH₃ | N | mp: 84–86° C. (E; E) |
| I.252 | CH₂CH=CH₂ | 2-F | H | 4 | CH₃ | OCH₃ | N | mp: 107–109° C. (E; E) |
| I.253 | CH₃ | 2-Br | H | 4 | CH₃ | OCH₃ | N | mp: 90–91° C. (E; E) |
| I.254 | C₂H₅ | 2-Br | H | 4 | CH₃ | OCH₃ | N | mp: 103–104° C. (E; E) |
| I.255 | (CH₂)₂CH₃ | 2-Br | H | 4 | CH₃ | OCH₃ | N | mp: 86–87° C. (E; E) |
| I.256 | (CH₂)₃CH₃ | 2-Br | H | 4 | CH₃ | OCH₃ | N | mp: 68–69° C. (E; E) |
| I.257 | CH₂CH=CH₂ | 2-Br | H | 4 | CH₃ | OCH₃ | N | mp: 96–97° C. (E; E) |
| I.258 | CH₃ | 2-C₂H₅ | H | 4 | CH₃ | OCH₃ | N | mp: 64–66° C. (E; E) |
| I.259 | C₂H₅ | 2-C₂H₅ | H | 4 | CH₃ | OCH₃ | N | mp: 56–57° C. (E; E) |
| I.260 | (CH₂)₂CH₃ | 2-C₂H₅ | H | 4 | CH₃ | OCH₃ | N | mp: 52–53° C. (E; E) |
| I.261 | (CH₂)₃CH₃ | 2-C₂H₅ | H | 4 | CH₃ | OCH₃ | N | mp: 40–41° C. (E; E) |
| I.262 | CH₂CH=CH₂ | 2-C₂H₅ | H | 4 | CH₃ | OCH₃ | N | resin (E; E) |

-continued

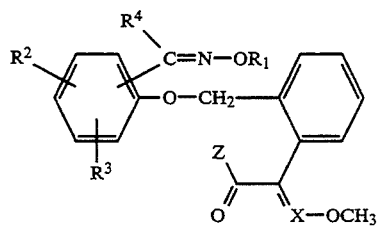

IA

| No. | R¹ | R² | R³ | P* | R⁴ | Z | X | Phys. data |
|---|---|---|---|---|---|---|---|---|
| I.263 | (CH$_2$)$_2$CH$_3$ | 2-Cl | 5-Cl | 4 | CH$_3$ | OCH$_3$ | N | mp: 80–81° C. (E; E) |
| I.264 | (CH$_2$)$_2$CH$_3$ | 2-Cl | 5-CH$_3$ | 4 | CH$_3$ | OCH$_3$ | N | mp: 56–58° C. (E; E) |
| I.265 | CH$_2$CH=CHCH$_3$ | H | H | 3 | H | OCH$_3$ | CH | mp: 74–76° C. (E; E) |
| I.266 | CH$_2$CH=CHCl | H | H | 3 | H | OCH$_3$ | CH | mp: 56–58° C. (E; E) |
| I.267 | CH$_2$CH(CH$_3$)$_2$ | H | H | 3 | H | OCH$_3$ | CH | mp: 52–54° C. (E; E) |
| I.268 | (CH$_2$)$_4$CH$_3$ | H | H | 3 | H | OCH$_3$ | CH | oil (E; E) |
| I.269 | CH$_2$C$_6$H$_5$ | H | H | 3 | CH$_3$ | OCH$_3$ | CH | oil (E; E) |
| I.270 | CH$_2$CH=CHCH$_3$ | H | H | 4 | H | OCH$_3$ | CH | mp: 86–88° C. (E; E) |
| I.271 | CH$_2$CH(CH$_3$)$_2$ | H | H | 4 | H | OCH$_3$ | CH | mp: 97–99° C. (E; E) |
| I.272 | (CH$_2$)$_4$CH$_3$ | H | H | 4 | H | OCH$_3$ | CH | mp: 84–86° C. (E; E) |
| I.273 | CH$_3$ | 2-CH$_3$ | H | 4 | CH$_3$ | OCH$_3$ | CH | mp: 118–120° C. (E; E) |
| I.274 | C$_2$H$_5$ | 2-CH$_3$ | H | 4 | CH$_3$ | OCH$_3$ | CH | mp: 101–103° C. (E; E) |
| I.275 | CH$_2$CH=CH$_2$ | 2-CH$_3$ | H | 4 | CH$_3$ | OCH$_3$ | CH | mp: 113–115° C. (E; E) |
| I.276 | (CH$_2$)$_2$CH$_3$ | 2-CH$_3$ | H | 4 | CH$_3$ | OCH$_3$ | CH | mp: 113–115° C. (E; E) |
| I.277 | CH(CH$_3$)$_2$ | 2-CH$_3$ | H | 4 | CH$_3$ | OCH$_3$ | CH | mp: 81–82° C. (E; E) |
| I.278 | CH(CH$_3$)$_2$ | 2-CH$_3$ | H | 4 | CH$_3$ | OCH$_3$ | N | mp: 80–81° C. (E; E) |
| I.279 | CH$_2$CH(CH$_3$)$_2$ | 2-CH$_3$ | H | 4 | CH$_3$ | OCH$_3$ | CH | mp: 117–119° C. (E; E) |
| I.280 | CH$_2$CH(CH$_3$)$_2$ | 2-CH$_3$ | H | 4 | CH$_3$ | OCH$_3$ | N | mp: 91–93° C. (E; E) |
| I.281 | (CH$_2$)$_2$CH$_3$ | 2-CH$_3$ | H | 4 | CH$_3$ | OCH$_3$ | CH | mp: 97–99° C. (E; E) |
| I.282 | C(CH$_3$)$_3$ | 2-CH$_3$ | H | 4 | CH$_3$ | OCH$_3$ | CH | mp: 83–85° C. (E; E) |
| I.283 | C(CH$_3$)$_3$ | 2-CH$_3$ | H | 4 | CH$_3$ | OCH$_3$ | N | mp: 86–88° C. (E; E) |
| I.284 | CH$_2$C(CH$_3$)=CH$_2$ | 2-CH$_3$ | H | 4 | CH$_3$ | OCH$_3$ | CH | mp: 106–108° C. (E; E) |
| I.285 | CH$_2$C(CH$_3$)=CH$_2$ | 2-CH$_3$ | H | 4 | CH$_3$ | OCH$_3$ | N | mp: 51–54° C. (E; E) |
| I.286 | (CH$_2$)$_2$CH(CH$_3$)$_2$ | 2-CH$_3$ | H | 4 | CH$_3$ | OCH$_3$ | CH | mp: 72–74° C. (E; E) |
| I.287 | (CH$_2$)$_2$CH(CH$_3$)$_2$ | 2-CH$_3$ | H | 4 | CH$_3$ | OCH$_3$ | N | mp: 58–60° C. (E; E) |
| I.288 | (CH$_2$)$_5$CH$_3$ | 2-CH$_3$ | H | 4 | CH$_3$ | OCH$_3$ | CH | mp: 76–78° C. (E; E) |
| I.289 | (CH$_2$)$_5$CH$_3$ | 2-CH$_3$ | H | 4 | CH$_3$ | OCH$_3$ | N | mp: 78–80° C. (E; E) |
| I.290 | CH$_2$C$_6$H$_5$ | 2-CH$_3$ | H | 4 | CH$_3$ | OCH$_3$ | CH | mp: 85–88° C. (E; E) |
| I.291 | CH$_2$C$_6$H$_5$ | 2-CH$_3$ | H | 4 | CH$_3$ | OCH$_3$ | N | mp: 98–101° C. (E; E) |
| I.292 | CH$_3$ | 2-CH$_3$ | 5-CH$_3$ | 4 | CH$_3$ | OCH$_3$ | CH | mp: 86–89° C. (E; E) |
| I.293 | CH$_2$CH=CH$_2$ | 2-CH$_3$ | 5-CH$_3$ | 4 | CH$_3$ | OCH$_3$ | CH | resin (E; E) |
| I.294 | CH(CH$_3$)$_2$ | 2-CH$_3$ | 5-CH$_3$ | 4 | CH$_3$ | OCH$_3$ | N | mp: 83–88° C. (E; E) |
| I.295 | CH(CH$_3$)$_2$ | 2-CH$_3$ | 5-CH$_3$ | 4 | CH$_3$ | OCH$_3$ | CH | mp: 90–92° C. (E; E) |
| I.296 | (CH$_2$)$_3$CH$_3$ | 2-CH$_3$ | 5-CH$_3$ | 4 | CH$_3$ | OCH$_3$ | CH | mp: 50–52° C. (E; E) |
| I.297 | CH$_2$C$_6$H$_5$ | 2-CH$_3$ | 5-CH$_3$ | 4 | CH$_3$ | OCH$_3$ | CH | resin (E; E) |
| I.298 | CH$_2$C$_6$H$_5$ | 2-CH$_3$ | 5-CH$_3$ | 4 | CH$_3$ | OCH$_3$ | N | mp: 41–43° C. (E; E) |
| I.299 | CH$_3$ | 3-C(CH$_3$)$_3$ | 5-CH$_3$ | 4 | CH$_3$ | OCH$_3$ | CH | resin (E; E) |
| I.300 | CH$_3$ | 3-C(CH$_3$)$_3$ | 5-CH$_3$ | 4 | CH$_3$ | OCH$_3$ | N | mp: 82–86° C. (E; E) |
| I.301 | CH$_3$ | 2-CH$_3$ | H | 4 | C$_2$H$_5$ | OCH$_3$ | CH | mp: 65–67° C. (E; E) |
| I.302 | CH$_2$CH=CH$_2$ | 2-CH$_3$ | H | 4 | C$_2$H$_5$ | OCH$_3$ | CH | mp: 83–86° C. (E; E) |
| I.303 | CH(CH$_3$)$_2$ | 2-CH$_3$ | H | 4 | C$_2$H$_5$ | OCH$_3$ | CH | mp: 92–94° C. (E; E) |
| I.304 | CH(CH$_3$)$_2$ | 2-CH$_3$ | H | 4 | C$_2$H$_5$ | OCH$_3$ | N | mp: 96–98° C. (E; E) |
| I.305 | CH$_3$ | 2-CH$_3$ | H | 4 | (CH$_2$)$_2$CH$_3$ | OCH$_3$ | CH | mp: 50–52° C. (E; E) |
| I.306 | CH$_3$ | 2-CH$_3$ | H | 4 | CH(CH$_3$)$_2$ | OCH$_3$ | N | mp: 73–75° C. (E; E) |
| I.307 | C$_2$H$_5$ | 2-CH$_3$ | 5-CH$_3$ | 4 | CH$_3$ | OCH$_3$ | CH | resin (E; E) |
| I.308 | C$_2$H$_5$ | 2-CH$_3$ | H | 4 | C$_2$H$_5$ | OCH$_3$ | CH | mp: 52–55° C. (E; E) |
| I.309 | (CH$_2$)$_2$CH$_3$ | 2-CH$_3$ | 5-CH$_3$ | 4 | CH$_3$ | OCH$_3$ | CH | resin (E; E) |
| I.310 | (CH$_2$)$_2$CH$_3$ | 2-CH$_3$ | 5-CH$_3$ | 4 | C$_2$H$_5$ | OCH$_3$ | CH | mp: 85–87° C. (E; E) |

P* = position of the group —CR⁴=NOR¹ relative to the —OCH$_2$ bridge
c-C$_3$H$_5$ = cyclopropyl Table 1: Compounds of the general formula I.1, in which the combination of the substituents R¹, R², R³, R⁴ and X for a compound corresponds to a line in Table A Table 2: Compounds of the general formula I.2, in which the combination of the substituents R¹, R², R³, R⁴ and X for a compound corresponds to a line in Table B

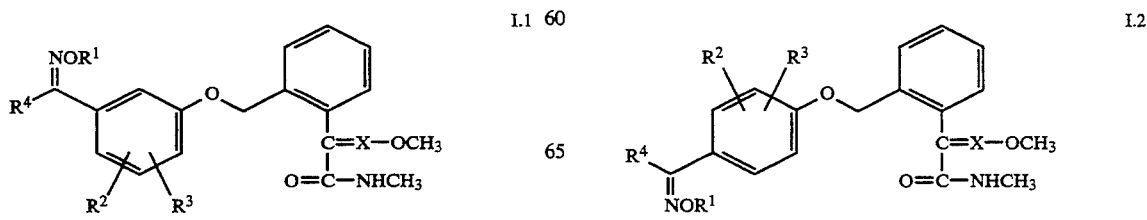

Table 3: Compounds of the general formula I.3, in which the combination of the substituents $R^1$, $R^2$, $R^3$, $R^4$ and X for a compound corresponds to a line in Table A

I.3

Table 4: Compounds of the general formula I.4, in which the combination of the substituents $R^1$, $R^2$, $R^3$, $R^4$ and X for a compound corresponds to a line in Table B

I.4

Table 5: Compounds of the general formula I.5, in which the combination of the substituents $R^1$, $R^2$, $R^3$, $R^4$, $R^5$, $R^6$ and X for a compound corresponds to a line in Table C

I.5

Table 6: Compounds of the general formula I.2, in which $R^4$ is cyclopropyl and the combination of the substituents $R^1$, $R^2$, $R^3$ and X for a compound corresponds to a line in Table D Table 7: Compounds of the general formula I.2, in which $R^4$ is cyclopentyl and the combination of the substituents $R^1$, $R^2$, $R^3$ and X for a compound corresponds to a line in Table D Table 8: Compounds of the general formula I.2, in which $R^4$ is cyclohexyl and the combination of the substituents $R^1$, $R^2$, $R^3$ and X for a compound corresponds to a line in Table D Table 9: Compounds of the general formula I.2, in which $R^4$ is $CF_3$ and the combination of the substituents $R^1$, $R^2$, $R^3$ and X for a compound corresponds to a line in Table D Table 10: Compounds of the general formula I.2, in which $R^4$ is $CH_2Cl$ and the combination of the substituents $R^1$, $R^2$, $R^3$ and X for a compound corresponds to a line in Table D Table 11: Compounds of the general formula I.2, in which $R^4$ is $CH_2CH_2Cl$ and the combination of the substituents $R^1$, $R^2$, $R^3$ and X for a compound corresponds to a line in Table D Table 12: Compounds of the general formula I.4, in which $R^4$ is cyclopropyl and the combination of the substituents $R^1$, $R^2$, $R^3$ and X for a compound corresponds to a line in Table D Table 13: Compounds of the general formula I.4, in which $R^4$ is cyclopentyl and the combination of the substituents $R^1$, $R^2$, $R^3$ and X for a compound corresponds to a line in Table D Table 14: Compounds of the general formula I.4, in which $R^4$ is cyclohexyl and the combination of the substituents $R^1$, $R^2$, $R^3$ and X for a compound corresponds to a line in Table D Table 15: Compounds of the general formula I.4, in which $R^4$ is $CF_3$ and the combination of the substituents $R^1$, $R^2$, $R^3$ and X for a compound corresponds to a line in Table D Table 16: Compounds of the general formula I.4, in which $R^4$ is $CH_2Cl$ and the combination of the substituents $R^1$, $R^2$, $R^3$ and X for a compound corresponds to a line in Table D Table 17: Compounds of the general formula I.4, in which $R^4$ is $CH_2CH_2Cl$ and the combination of the substituents $R^1$, $R^2$, $R^3$ and X for a compound corresponds to a line in Table D Table 18: Compounds of the general formula I.2, in which $R^4$ is cyclopropyl, =X— is =N— and the combination of the substituents $R^1$, $R^2$ and $R^3$ for a compound corresponds to a line in Table E Table 19: Compounds of the general formula I.2, in which $R^4$ is cyclopentyl, =X— is =N— and the combination of the substituents $R^1$, $R^2$ and $R^3$ for a compound corresponds to a line in Table E Table 20: Compounds of the general formula I.2, in which $R^4$ is cyclohexyl, =X— is =N— and the combination of the substituents $R^1$, $R^2$ and $R^3$ for a compound corresponds to a line in Table E Table 21: Compounds of the general formula I.2, in which $R^4$ is $CF_3$, =X— is =N— and the combination of the substituents $R^1$, $R^2$ and $R^3$ for a compound corresponds to a line in Table E Table 22: Compounds of the general formula I.2, in which $R^4$ is $CH_2CH_2Cl$, =X— is =N— and the combination of the substituents $R^1$, $R^2$ and $R^3$ for a compound corresponds to a line in Table E Table 23: Compounds of the general formula I.4, in which $R^4$ is cyclopropyl, =X— is =N— and the combination of the substituents $R^1$, $R^2$ and $R^3$ for a compound corresponds to a line in Table E Table 24: Compounds of the general formula I.4, in which $R^4$ is cyclopentyl, =X— is =N— and the combination of the substituents $R^1$, $R^2$ and $R^3$ for a compound corresponds to a line in Table E Table 25: Compounds of the general formula I.4, in which $R^4$ is cyclohexyl, =X— is =N— and the combination of the substituents $R^1$, $R^2$ and $R^3$ for a compound corresponds to a line in Table E Table 26: Compounds of the general formula I.4, in which $R^4$ is $CF_3$, =X— is =N— and the combination of the substituents $R^1$, $R^2$ and $R^3$ for a compound corresponds to a line in Table E Table 27: Compounds of the general formula I.4, in which $R^4$ is $CH_2CH_2Cl$, =X— is =N— and the combination of the substituents $R^1$, $R^2$ and $R^3$ for a compound corresponds to a line in Table E

TABLE A

| Comp. no. | $R^1$ | $R^2$ | $R^3$ | $R^4$ | X |
|---|---|---|---|---|---|
| A.001 | $CH_3-$ | H | H | H | CH |
| A.002 | $CH_3-$ | H | H | H | N |
| A.003 | $CH_3-$ | 2-Cl | 5-Cl | H | CH |
| A.004 | $CH_3-$ | 2-Cl | 5-Cl | H | N |
| A.005 | $CH_3-$ | 4-Cl | H | H | CH |
| A.006 | $CH_3-$ | 4-Cl | H | H | N |
| A.007 | $CH_3-$ | $4-CH_3$ | H | H | CH |
| A.008 | $CH_3-$ | $4-CH_3$ | H | H | N |
| A.009 | $CH_3-$ | $5-OCH_3$ | H | H | CH |
| A.010 | $CH_3-$ | $5-OCH_3$ | H | H | N |
| A.011 | $CH_3-$ | $6-OCH_3$ | H | H | CH |
| A.012 | $CH_3-$ | $6-OCH_3$ | H | H | N |
| A.013 | $CH_3-$ | H | H | H | CH |
| A.014 | $CH_3-CH_2-$ | H | H | H | N |
| A.015 | $CH_3-CH_2-$ | 2-Cl | 5-Cl | H | CH |
| A.016 | $CH_3-CH_2-$ | 2-Cl | 5-Cl | H | N |
| A.017 | $CH_3-CH_2-$ | 4-Cl | H | H | CH |
| A.018 | $CH_3-CH_2-$ | 4-Cl | H | H | N |
| A.019 | $CH_3-CH_2-$ | $4-CH_3$ | H | H | CH |
| A.020 | $CH_3-CH_2-$ | $4-CH_3$ | H | H | N |
| A.021 | $CH_3-CH_2-$ | $5-OCH_3$ | H | H | CH |
| A.022 | $CH_3-CH_2-$ | $5-OCH_3$ | H | H | N |
| A.023 | $CH_3-CH_2-$ | $6-OCH_3$ | H | H | CH |
| A.024 | $CH_3-CH_2-$ | $6-OCH_3$ | H | H | N |
| A.025 | $CH_3-CH_2-CH_2-$ | H | H | H | CH |
| A.026 | $CH_3-CH_2-CH_2-$ | H | H | H | N |
| A.027 | $CH_2=CH-CH_2-$ | H | H | H | CH |
| A.028 | $CH_2=CH-CH_2-$ | H | H | H | N |
| A.029 | $CH_3-CH(CH_3)-$ | H | H | H | CH |
| A.030 | $CH_3-CH(CH_3)-$ | H | H | H | N |
| A.031 | $HC\equiv C-CH_2-$ | H | H | H | CH |
| A.032 | $HC\equiv C-CH_2-$ | H | H | H | N |
| A.033 | cyclo-$C_3H_5-CH_2-$ | H | H | H | CH |
| A.034 | cyclo-$C_3H_5-CH_2-$ | H | H | H | N |
| A.035 | $CH_3-CH_2-CH_2-CH_2-$ | H | H | H | CH |
| A.036 | $CH_3-CH_2-CH_2-CH_2-$ | H | H | H | N |
| A.037 | $CH_3-CH=CH-CH_2-$ | H | H | H | CH |
| A.038 | $CH_3-CH=CH-CH_2-$ | H | H | H | N |
| A.039 | $CH_3-(CH_2)_5-$ | H | H | H | CH |
| A.040 | $CH_3-(CH_2)_5-$ | H | H | H | N |
| A.041 | cyclo-$C_6H_{11}-$ | H | H | H | CH |
| A.042 | cyclo-$C_6H_{11}-$ | H | H | H | N |
| A.043 | $C_6H_5-CH_2-$ | H | H | H | CH |
| A.044 | $C_6H_5-CH_2-$ | H | H | H | N |
| A.045 | $4-Cl-C_6H_4-CH_2-$ | H | H | H | CH |
| A.046 | $4-Cl-C_6H_4-CH_2-$ | H | H | H | N |
| A.047 | $3-CF_3-C_6H_4-CH_2-$ | H | H | H | CH |
| A.048 | $3-CF_3-C_6H_4-CH_2-$ | H | H | H | N |
| A.049 | $4-Cl-C_6H_4-CH_2-CH_2-$ | H | H | H | CH |
| A.050 | $4-Cl-C_6H_4-CH_2-CH_2-$ | H | H | H | N |
| A.051 | $C_6H_5-CH_2-CH_2-CH_2-$ | H | H | H | CH |
| A.052 | $C_6H_5-CH_2-CH_2-CH_2-$ | H | H | H | N |
| A.053 | $C_6H_5-(CH_2)_4-$ | H | H | H | CH |
| A.054 | $C_6H_5-(CH_2)_4-$ | H | H | H | N |
| A.055 | $C_6H_5-CH_2-CH=CH-CH_2-$ | H | H | H | CH |
| A.056 | $C_6H_5-CH_2-CH=CH-CH_2-$ | H | H | H | N |
| A.057 | $4-F-C_6H_4-CH=CH-CH_2-CH_2-$ | H | H | H | CH |
| A.058 | $4-F-C_6H_4-CH=CH-CH_2-CH_2-$ | H | H | H | N |
| A.059 | $t-C_4H_9O-CO-CH_2-$ | H | H | H | CH |
| A.060 | $t-C_4H_9O-CO-CH_2-$ | H | H | H | N |
| A.061 | $t-C_4H_9O-CO-(CH_2)_3-$ | H | H | H | CH |
| A.062 | $t-C_4H_9O-CO-(CH_2)_3-$ | H | H | H | N |
| A.063 | $Cl-CH=CH-CH_2-$ | H | H | H | CH |
| A.064 | $Cl-CH=CH-CH_2-$ | H | H | H | N |
| A.065 | $C_2H_5$ | $6-OC_2H_5$ | H | H | CH |
| A.066 | $C_2H_5$ | $6-OC_2H_5$ | H | H | N |
| A.067 | $CH_3-C(CH_3)_2-$ | H | H | H | CH |
| A.068 | $CH_3-C(CH_3)_2-$ | H | H | H | N |
| A.069 | $CH_3-CH(CH_3)-CH_2-$ | H | H | H | CH |
| A.070 | $CH_3-CH(CH_3)-CH_2-$ | H | H | H | N |
| A.071 | $CH_2=C(CH_3)-CH_2$ | H | H | H | CH |
| A.072 | $CH_2=C(CH_3)-CH_2$ | H | H | H | N |
| A.073 | $CH_3-CH(CH_3)-CH_2-CH_2-$ | H | H | H | CH |
| A.074 | $CH_3-CH(CH_3)-CH_2-CH_2-$ | H | H | H | N |
| A.075 | $CH_3-(CH_2)_4-$ | H | H | H | CH |
| A.076 | $CH_3-(CH_2)_4-$ | H | H | H | N |
| A.077 | $2-F-C_6H_4-CH_2-$ | H | H | H | CH |
| A.078 | $2-F-C_6H_4-CH_2-$ | H | H | H | N |
| A.079 | $3-F-C_6H_4-CH_2-$ | H | H | H | CH |
| A.080 | $3-F-C_6H_4-CH_2-$ | H | H | H | N |
| A.081 | $2-Cl-C_6H_4-CH_2-$ | H | H | H | CH |

TABLE A-continued

| Comp. no. | R¹ | R² | R³ | R⁴ | X |
|---|---|---|---|---|---|
| A.082 | 2-Cl—C₆H₄—CH₂— | H | H | H | N |
| A.083 | 3,4-Cl₂—C₆H₃—CH₂— | H | H | H | CH |
| A.084 | 3,4-Cl₂—C₆H₃—CH₂— | H | H | H | N |
| A.085 | 2,6-Cl₂—C₆H₃—CH₂— | H | H | H | CH |
| A.086 | 2,6-Cl₂—C₆H₃—CH₂— | H | H | H | N |
| A.087 | C₆H₅—CH₂—CH₂— | H | H | H | CH |
| A.088 | C₆H₅—CH₂—CH₂— | H | H | H | N |
| A.089 | C₆H₅—CH=CH—CH₂—CH₂— | H | H | H | CH |
| A.090 | C₆H₅—CH=CH—CH₂—CH₂— | H | H | H | N |
| A.091 | 4-Cl—C₆H₄—CH₂—CH=CH—CH₂— | H | H | H | CH |
| A.092 | 4-Cl—C₆H₄—CH₂—CH=CH—CH₂— | H | H | H | N |
| A.093 | 4-CF₃—C₆H₄—CH₂—CH=CH—CH₂— | H | H | H | CH |
| A.094 | 4-CF₃—C₆H₄—CH₂—CH=CH—CH₂— | H | H | H | N |
| A.095 | CH₃ | H | H | CH₃ | CH |
| A.096 | CH₃ | H | H | CH₃ | N |
| A.097 | CH₃ | 2-Cl | 5-Cl | CH₃ | CH |
| A.098 | CH₃ | 2-Cl | 5-Cl | CH₃ | N |
| A.099 | CH₃ | 4-Cl | H | CH₃ | CH |
| A.100 | CH₃ | 4-Cl | H | CH₃ | N |
| A.101 | CH₃ | 4-CH₃ | H | CH₃ | CH |
| A.102 | CH₃ | 4-CH₃ | H | CH₃ | N |
| A.103 | CH₃ | 5-OCH₃ | H | CH₃ | CH |
| A.104 | CH₃ | 5-OCH₃ | H | CH₃ | N |
| A.105 | CH₃ | 6-OCH₃ | H | CH₃ | CH |
| A.106 | CH₃ | 6-OCH₃ | H | CH₃ | N |
| A.107 | CH₃—CH₂ | H | H | CH₃ | CH |
| A.108 | CH₃—CH₂ | H | H | CH₃ | N |
| A.109 | CH₃—CH₂ | 2-Cl | 5-Cl | CH₃ | CH |
| A.110 | CH₃—CH₂ | 2-Cl | 5-Cl | CH₃ | N |
| A.111 | CH₃—CH₂ | 4-Cl | H | CH₃ | CH |
| A.112 | CH₃—CH₂ | 4-Cl | H | CH₃ | N |
| A.113 | CH₃—CH₂ | 4-CH₃ | H | CH₃ | CH |
| A.114 | CH₃—CH₂ | 4-CH₃ | H | CH₃ | N |
| A.115 | CH₃—CH₂ | 5-OCH₃ | H | CH₃ | CH |
| A.116 | CH₃—CH₂ | 5-OCH₃ | H | CH₃ | N |
| A.117 | CH₃—CH₂ | 6-OCH₃ | H | CH₃ | CH |
| A.118 | CH₃—CH₂ | 6-OCH₃ | H | CH₃ | N |
| A.119 | CH₃—CH₂—CH₂ | H | H | CH₃ | CH |
| A.120 | CH₃—CH₂—CH₂ | H | H | CH₃ | N |
| A.121 | CH₂=CH—CH₂ | H | H | CH₃ | CH |
| A.122 | CH₂=CH—CH₂ | H | H | CH₃ | N |
| A.123 | CH₃—CH(CH₃) | H | H | CH₃ | CH |
| A.124 | CH₃—CH(CH₃) | H | H | CH₃ | N |
| A.125 | HC≡C—CH₂ | H | H | CH₃ | CH |
| A.126 | HC≡C—CH₂ | H | H | CH₃ | N |
| A.127 | cyclo-C₃H₅—CH₂ | H | H | CH₃ | CH |
| A.128 | cyclo-C₃H₅—CH₂ | H | H | CH₃ | N |
| A.129 | CH₃—CH₂—CH₂—CH₂ | H | H | CH₃ | CH |
| A.130 | CH₃—CH₂—CH₂—CH₂ | H | H | CH₃ | N |
| A.131 | CH₃—CH=CH—CH₂ | H | H | CH₃ | CH |
| A.132 | CH₃—CH=CH—CH₂ | H | H | CH₃ | N |
| A.133 | CH₃—(CH₂)₅ | H | H | CH₃ | CH |
| A.134 | CH₃—(CH₂)₅ | H | H | CH₃ | N |
| A.135 | cyclo-C₆H₁₁ | H | H | CH₃ | CH |
| A.136 | cyclo-C₆H₁₁ | H | H | CH₃ | N |
| A.137 | C₆H₅—CH₂ | H | H | CH₃ | CH |
| A.138 | C₆H₅—CH₂ | H | H | CH₃ | N |
| A.139 | 4-Cl-C₆H₄—CH₂ | H | H | CH₃ | CH |
| A.140 | 4-Cl-C₆H₄—CH₂ | H | H | CH₃ | N |
| A.141 | 3-CF₃—C₆H₄—CH₂ | H | H | CH₃ | CH |
| A.142 | 3-CF₃—C₆H₄—CH₂ | H | H | CH₃ | N |
| A.143 | 4-Cl—C₆H₄—CH₂—CH₂ | H | H | CH₃ | CH |
| A.144 | 4-Cl—C₆H₄—CH₂—CH₂ | H | H | CH₃ | N |
| A.145 | C₆H₅—CH₂—CH₂—CH₂ | H | H | CH₃ | CH |
| A.146 | C₆H₅—CH₂—CH₂—CH₂ | H | H | CH₃ | N |
| A.147 | C₆H₅—(CH₂)₄ | H | H | CH₃ | CH |
| A.148 | C₆H₅—(CH₂)₄ | H | H | CH₃ | N |
| A.149 | C₆H₅—CH₂—CH=CH—CH₂ | H | H | CH₃ | CH |
| A.150 | C₆H₅—CH₂—CH=CH—CH₂ | H | H | CH₃ | N |
| A.151 | 4-F—C₆H₄—CH=CH—CH₂—CH₂ | H | H | CH₃ | CH |
| A.152 | 4-F—C₆H₄—CH=CH—CH₂—CH₂ | H | H | CH₃ | N |
| A.153 | t-C₄H₉O—CO—CH₂ | H | H | CH₃ | CH |
| A.154 | t-C₄H₉O—CO—CH₂ | H | H | CH₃ | N |
| A.155 | t-C₄H₉O—CO—(CH₂)₃ | H | H | CH₃ | CH |
| A.156 | t-C₄H₉O—CO—(CH₂)₃ | H | H | CH₃ | N |
| A.157 | Cl—CH=CH—CH₂ | H | H | CH₃ | CH |
| A.158 | Cl—CH=CH—CH₂ | H | H | CH₃ | N |
| A.159 | C₂H₅ | 6-OC₂H₅ | H | CH₃ | CH |
| A.160 | C₂H₅ | 6-OC₂H₅ | H | CH₃ | N |
| A.161 | CH₃—C(CH₂)₂ | H | H | CH₃ | CH |
| A.162 | CH₃—C(CH₂)₂ | H | H | CH₃ | N |

TABLE A-continued

| Comp. no. | R$^1$ | R$^2$ | R$^3$ | R$^4$ | X |
|---|---|---|---|---|---|
| A.163 | CH$_3$—CH(CH$_3$)—CH$_2$ | H | H | CH$_3$ | CH |
| A.164 | CH$_3$—CH(CH$_3$)—CH$_2$ | H | H | CH$_3$ | N |
| A.165 | CH$_2$=C(CH$_3$)—CH$_2$ | H | H | CH$_3$ | CH |
| A.166 | CH$_2$=C(CH$_3$)—CH$_2$ | H | H | CH$_3$ | N |
| A.167 | CH$_3$—CH(CH$_3$)—CH$_2$—CH$_2$ | H | H | CH$_3$ | CH |
| A.168 | CH$_3$—CH(CH$_3$)—CH$_2$—CH$_2$ | H | H | CH$_3$ | N |
| A.169 | CH$_3$—(CH$_2$)$_4$ | H | H | CH$_3$ | CH |
| A.170 | CH$_3$—(CH$_2$)$_4$ | H | H | CH$_3$ | N |
| A.171 | 2-F—C$_6$H$_4$—CH$_2$ | H | H | CH$_3$ | CH |
| A.172 | 2-F—C$_6$H$_4$—CH$_2$ | H | H | CH$_3$ | N |
| A.173 | 3-F—C$_6$H$_4$—CH$_2$ | H | H | CH$_3$ | CH |
| A.174 | 3-F—C$_6$H$_4$—CH$_2$ | H | H | CH$_3$ | N |
| A.175 | 2-Cl—C$_6$H$_4$—CH$_2$ | H | H | CH$_3$ | CH |
| A.176 | 2-Cl—C$_6$H$_4$—CH$_2$ | H | H | CH$_3$ | N |
| A.177 | 3,4-Cl$_2$—C$_6$H$_3$—CH$_2$ | H | H | CH$_3$ | CH |
| A.178 | 3,4-Cl$_2$—C$_6$H$_3$—CH$_2$ | H | H | CH$_3$ | N |
| A.179 | 2,6-Cl$_2$—C$_6$H$_3$—CH$_2$ | H | H | CH$_3$ | CH |
| A.180 | 2,6-Cl$_2$—C$_6$H$_3$—CH$_2$ | H | H | CH$_3$ | N |
| A.181 | C$_6$H$_5$—CH$_2$—CH$_2$ | H | H | CH$_3$ | CH |
| A.182 | C$_6$H$_5$—CH$_2$—CH$_2$ | H | H | CH$_3$ | N |
| A.183 | C$_6$H$_5$—CH=CH—CH$_2$—CH$_2$ | H | H | CH$_3$ | CH |
| A.184 | C$_6$H$_5$—CH=CH—CH$_2$—CH$_2$ | H | H | CH$_3$ | N |
| A.185 | 4-Cl-C$_6$H$_4$—CH$_2$CH=CH—CH$_2$ | H | H | CH$_3$ | CH |
| A.186 | 4-Cl-C$_6$H$_4$—CH$_2$CH=CH—CH$_2$ | H | H | CH$_3$ | N |
| A.187 | 4-CF$_3$—C$_6$H$_4$—CH$_2$—CH=CH—CH$_2$ | H | H | CH$_3$ | CH |
| A.188 | 4-CF$_3$—C$_6$H$_4$—CH$_2$—CH=CH—CH$_2$ | H | H | CH$_3$ | N |
| A.189 | CH$_3$ | H | H | C$_6$H$_5$ | CH |
| A.190 | CH$_3$ | H | H | C$_6$H$_5$ | N |
| A.191 | C$_2$H$_5$ | H | H | C$_6$H$_5$ | CH |
| A.192 | C$_2$H$_5$ | H | H | C$_6$H$_5$ | N |
| A.193 | CH$_3$—CH$_2$—CH$_2$ | H | H | C$_6$H$_5$ | CH |
| A.194 | CH$_3$—CH$_2$—CH$_2$ | H | H | C$_6$H$_5$ | N |
| A.195 | CH$_3$—(CH$_2$)$_5$ | H | H | C$_6$H$_5$ | CH |
| A.196 | CH$_3$—(CH$_2$)$_5$ | H | H | C$_6$H$_5$ | N |
| A.197 | C$_6$H$_5$—CH$_2$ | H | H | C$_6$H$_5$ | CH |
| A.198 | C$_6$H$_5$—CH$_2$ | H | H | C$_6$H$_5$ | N |

TABLE B

| Comp. no. | R$^1$ | R$^2$ | R$^3$ | R$^4$ | X |
|---|---|---|---|---|---|
| B.001 | CH$_3$— | H | H | H | CH |
| B.002 | CH$_3$— | H | H | H | N |
| B.003 | CH$_3$— | 2-Cl | H | H | CH |
| B.004 | CH$_3$— | 2-Cl | H | H | N |
| B.005 | CH$_3$— | 2-CH$_3$ | H | H | CH |
| B.006 | CH$_3$— | 2-CH$_3$ | H | H | N |
| B.007 | CH$_3$— | 2-OCH$_3$ | H | H | CH |
| B.008 | CH$_3$— | 2-OCH$_3$ | H | H | N |
| B.009 | CH$_3$— | 3-Cl | H | H | CH |
| B.010 | CH$_3$— | 3-Cl | H | H | N |
| B.011 | CH$_3$— | 3-CH$_3$ | H | H | CH |
| B.012 | CH$_3$— | 3-CH$_3$ | H | H | N |
| B.013 | CH$_3$— | 3-OCH$_3$ | H | H | CH |
| B.014 | CH$_3$— | 3-OCH$_3$ | H | H | N |
| B.015 | CH$_3$ | 2-Cl | 6-Cl | H | CH |
| B.016 | CH$_3$ | 2-Cl | 6-Cl | H | N |
| B.017 | CH$_3$—CH$_2$— | H | H | H | CH |
| B.018 | CH$_3$—CH$_2$— | H | H | H | N |
| B.019 | CH$_3$—CH$_2$— | 2-Cl | H | H | CH |
| B.020 | CH$_3$—CH$_2$— | 2-Cl | H | H | N |
| B.021 | CH$_3$—CH$_2$— | 2-CH$_3$ | H | H | CH |
| B.022 | CH$_3$—CH$_2$— | 2-CH$_3$ | H | H | N |
| B.023 | CH$_3$—CH$_2$— | 2-OCH$_3$ | H | H | CH |
| B.024 | CH$_3$—CH$_2$— | 2-OCH$_3$ | H | H | N |
| B.025 | CH$_3$—CH$_2$— | 3-Cl | H | H | CH |
| B.026 | CH$_3$—CH$_2$— | 3-Cl | H | H | N |
| B.027 | CH$_3$—CH$_2$— | 3-CH$_3$ | H | H | CH |
| B.028 | CH$_3$—CH$_2$— | 3-CH$_3$ | H | H | N |
| B.029 | CH$_3$—CH$_2$— | 3-OCH$_3$ | H | H | CH |
| B.030 | CH$_3$—CH$_2$— | 3-OCH$_3$ | H | H | N |
| B.031 | CH$_3$—CH$_2$— | 2-Cl | H | H | CH |
| B.032 | CH$_3$—CH$_2$— | 2-Cl | 6-Cl | H | N |
| B.033 | CH$_3$—CH$_2$—CH$_2$— | H | 6-Cl | H | CH |
| B.034 | CH$_3$—CH$_2$—CH$_2$— | H | H | H | N |
| B.035 | CH$_2$=CH—CH$_2$— | H | H | H | CH |
| B.036 | CH$_2$=CH—CH$_2$— | H | H | H | N |
| B.037 | CH$_3$—CH(CH$_3$)— | H | H | H | CH |
| B.038 | CH$_3$—CH(CH$_3$)— | H | H | H | N |

TABLE B-continued

| Comp. no. | R¹ | R² | R³ | R⁴ | X |
|---|---|---|---|---|---|
| B.039 | HC≡C—CH₂— | H | H | H | CH |
| B.040 | HC≡C—CH₂— | H | H | H | N |
| B.041 | cyclo-C₃H₅—CH₂— | H | H | H | CH |
| B.042 | cyclo-C₃H₅—CH₂— | H | H | H | N |
| B.043 | CH₃—CH₂—CH₂—CH₂— | H | H | H | CH |
| B.044 | CH₃—CH₂—CH₂—CH₂— | H | H | H | N |
| B.045 | CH₃—CH=CH—CH₂— | H | H | H | CH |
| B.046 | CH₃—CH=CH—CH₂— | H | H | H | N |
| B.047 | CH₃—(CH₂)₅— | H | H | H | CH |
| B.048 | CH₃—(CH₂)₅— | H | H | H | N |
| B.049 | cyclo-C₆H₁₁— | H | H | H | CH |
| B.050 | cyclo-C₆H₁₁— | H | H | H | N |
| B.051 | C₆H₅—CH₂— | H | H | H | CH |
| B.052 | C₆H₅—CH₂— | H | H | H | N |
| B.053 | 4-Cl—C₆H₄—CH₂— | H | H | H | CH |
| B.054 | 4-Cl—C₆H₄—CH₂— | H | H | H | N |
| B.055 | 3-CF₃—C₆H₄—CH₂— | H | H | H | CH |
| B.056 | 3-CF₃—C₆H₄—CH₂— | H | H | H | N |
| B.057 | 4-Cl—C₆H₄—CH₂— | H | H | H | CH |
| B.058 | 4-Cl—C₆H₄—CH₂— | H | H | H | N |
| B.059 | C₆H₅—CH₂—CH₂—CH₂— | H | H | H | CH |
| B.060 | C₆H₅—CH₂—CH₂—CH₂— | H | H | H | N |
| B.061 | C₆H₅—(CH₂)₄— | H | H | H | CH |
| B.062 | C₆H₅—(CH₂)₄— | H | H | H | N |
| B.063 | C₆H₅—CH₂—CH=CH—CH₂ | H | H | H | CH |
| B.064 | C₆H₅—CH₂—CH=CH—CH₂ | H | H | H | N |
| B.065 | 4-F—C₆H₄—CH=CHCH₂CH₂ | H | H | H | CH |
| B.066 | 4-F—C₆H₄—CH=CHCH₂CH₂ | H | H | H | N |
| B.067 | t-C₄H₉O—CO—CH₂— | H | H | H | CH |
| B.068 | t-C₄H₉O—CO—CH₂— | H | H | H | N |
| B.069 | t-C₄H₉O—CO—(CH₂)₃— | H | H | H | CH |
| B.070 | t-C₄H₉O—CO—(CH₂)₃— | H | H | H | N |
| B.071 | Cl—CH=CH—CH₂— | H | H | H | CH |
| B.072 | Cl—CH=CH—CH₂— | H | H | H | N |
| B.073 | C₂H₅ | 6-OC₂H₅ | H | H | CH |
| B.074 | C₂H₅ | 6-OC₂H₅ | H | H | N |
| B.075 | CH₃—C(CH₃)₂— | H | H | H | CH |
| B.076 | CH₃—C(CH₃)₂— | H | H | H | N |
| B.077 | CH₃—CH(CH₃)—CH₂— | H | H | H | CH |
| B.078 | CH₃—CH(CH₃)—CH₂— | H | H | H | N |
| B.079 | CH₂=C(CH₃)—CH₂— | H | H | H | CH |
| B.080 | CH₂=C(CH₃)—CH₂— | H | H | H | N |
| B.081 | CH₃—CH(CH₃)—CH₂CH₂ | H | H | H | CH |
| B.082 | CH₃—CH(CH₃)—CH₂CH₂ | H | H | H | N |
| B.083 | CH₃—(CH₂)₄— | H | H | H | CH |
| B.084 | CH₃—(CH₂)₄— | H | H | H | N |
| B.085 | 2-F—C₆H₄—CH₂— | H | H | H | CH |
| B.086 | 2-F—C₆H₄—CH₂— | H | H | H | N |
| B.087 | 3-F—C₆H₄—CH₂— | H | H | H | CH |
| B.088 | 3-F—C₆H₄—CH₂— | H | H | H | N |
| B.089 | 2-Cl—C₆H₄—CH₂— | H | H | H | CH |
| B.090 | 2-Cl—C₆H₄—CH₂— | H | H | H | N |
| B.091 | 3,4-Cl₂—C₆H₃—CH₂— | H | H | H | CH |
| B.092 | 3,4-Cl₂—C₆H₃—CH₂— | H | H | H | N |
| B.093 | 2,6-Cl₂—C₆H₃—CH₂— | H | H | H | CH |
| B.094 | 2,6-Cl₂—C₆H₃—CH₂— | H | H | H | N |
| B.095 | C₆H₅—CH₂—CH₂— | H | H | H | CH |
| B.096 | C₆H₅—CH₂—CH₂— | H | H | H | N |
| B.097 | C₆H₅—CH=CH—CH₂—CH₂— | H | H | H | CH |
| B.098 | C₆H₅—CH=CH—CH₂—CH₂— | H | H | H | N |
| B.099 | 4-Cl—C₆H₄—CH₂CH=CHCH₂ | H | H | H | CH |
| B.100 | 4-Cl—C₆H₄—CH₂CH=CHCH₂ | H | H | H | N |
| B.101 | 4-CF₃—C₆H₄—CH₂CH=CHCH₂ | H | H | H | CH |
| B.102 | 4-CF₃—C₆H₄—CH₂CH=CHCH₂ | H | H | H | N |
| B.103 | CH₃ | H | H | CH₃ | CH |
| B.104 | CH₃ | H | H | CH₃ | N |
| B.105 | CH₃ | 2-Cl | H | CH₃ | CH |
| B.106 | CH₃ | 2-Cl | H | CH₃ | N |
| B.107 | CH₃ | 2-CH₃ | H | CH₃ | CH |
| B.108 | CH₃ | 2-CH₃ | H | CH₃ | N |
| B.109 | CH₃ | 2-OCH₃ | H | CH₃ | CH |
| B.110 | CH₃ | 2-OCH₃ | H | CH₃ | N |

TABLE B-continued

| Comp. no. | R¹ | R² | R³ | R⁴ | X |
|---|---|---|---|---|---|
| B.111 | CH₃ | 3-Cl | H | CH₃ | CH |
| B.112 | CH₃ | 3-Cl | H | CH₃ | N |
| B.113 | CH₃ | 3-CH₃ | H | CH₃ | CH |
| B.114 | CH₃ | 3-CH₃ | H | CH₃ | N |
| B.115 | CH₃ | 3-OCH₃ | H | CH₃ | CH |
| B.116 | CH₃ | 3-OCH₃ | H | CH₃ | N |
| B.117 | CH₃ | 2-Cl | 6-Cl | CH₃ | CH |
| B.118 | CH₃ | 2-Cl | 6-Cl | CH₃ | N |
| B.119 | CH₃—CH₂ | H | H | CH₃ | CH |
| B.120 | CH₃—CH₂ | H | H | CH₃ | N |
| B.121 | CH₃—CH₂ | 2-Cl | H | CH₃ | CH |
| B.122 | CH₃—CH₂ | 2-Cl | H | CH₃ | N |
| B.123 | CH₃—CH₂ | 2-CH₃ | H | CH₃ | CH |
| B.124 | CH₃—CH₂ | 2-CH₃ | H | CH₃ | N |
| B.125 | CH₃—CH₂ | 2-OCH₃ | H | CH₃ | CH |
| B.126 | CH₃—CH₂ | 2-OCH₃ | H | CH₃ | N |
| B.127 | CH₃—CH₂ | 3-Cl | H | CH₃ | CH |
| B.128 | CH₃—CH₂ | 3-Cl | H | CH₃ | N |
| B.129 | CH₃—CH₂ | 3-CH₃ | H | CH₃ | CH |
| B.130 | CH₃—CH₂ | 3-CH₃ | H | CH₃ | N |
| B.131 | CH₃—CH₂ | 3-OCH₃ | H | CH₃ | CH |
| B.132 | CH₃—CH₂ | 3-OCH₃ | H | CH₃ | N |
| B.133 | CH₃—CH₂ | 2-Cl | 6-Cl | CH₃ | CH |
| B.134 | CH₃—CH₂ | 2-Cl | 6-Cl | CH₃ | N |
| B.135 | CH₃—CH₂—CH₂ | H | H | CH₃ | CH |
| B.136 | CH₃—CH₂—CH₂ | H | H | CH₃ | N |
| B.137 | CH₂=CH—CH₂ | H | H | CH₃ | CH |
| B.138 | CH₂=CH—CH₂ | H | H | CH₃ | N |
| B.139 | CH₃—CH(CH₃) | H | H | CH₃ | CH |
| B.140 | CH₃—CH(CH₃) | H | H | CH₃ | N |
| B.141 | HC≡C—CH₂ | H | H | CH₃ | CH |
| B.142 | HC≡C—CH₂ | H | H | CH₃ | N |
| B.143 | cyclo-C₃H₅—CH₂ | H | H | CH₃ | CH |
| B.144 | cyclo-C₃H₅—CH₂ | H | H | CH₃ | N |
| B.145 | CH₃—CH₂—CH₂—CH₂ | H | H | CH₃ | CH |
| B.146 | CH₃—CH₂—CH₂—CH₂ | H | H | CH₃ | N |
| B.147 | CH₃—CH=CH—CH₂ | H | H | CH₃ | CH |
| B.148 | CH₃—CH=CH—CH₂ | H | H | CH₃ | N |
| B.149 | CH₃—(CH₂)₅ | H | H | CH₃ | CH |
| B.150 | CH₃—(CH₂)₅ | H | H | CH₃ | N |
| B.151 | cyclo-C₆H₁₁ | H | H | CH₃ | CH |
| B.152 | cyclo-C₆H₁₁ | H | H | CH₃ | N |
| B.153 | C₆H₅—CH₂ | H | H | CH₃ | CH |
| B.154 | C₆H₅—CH₂ | H | H | CH₃ | N |
| B.155 | 4-Cl—C₆H₄—CH₂ | H | H | CH₃ | CH |
| B.156 | 4-Cl—C₆H₄—CH₂ | H | H | CH₃ | N |
| B.157 | 3-CF₃—C₆H₄—CH₂ | H | H | CH₃ | CH |
| B.158 | 3-CF₃—C₆H₄—CH₂ | H | H | CH₃ | N |
| B.159 | 4-Cl—C₆H₄—CH₂—CH₂ | H | H | CH₃ | CH |
| B.160 | 4-Cl—C₆H₄—CH₂—CH₂ | H | H | CH₃ | N |
| B.161 | C₆H₅—CH₂—CH₂—CH₂ | H | H | CH₃ | CH |
| B.162 | C₆H₅—CH₂—CH₂—CH₂ | H | H | CH₃ | N |
| B.163 | C₆H₅—(CH₂)₄ | H | H | CH₃ | CH |
| B.164 | C₆H₅—(CH₂)₄ | H | H | CH₃ | N |
| B.165 | C₆H₅—CH₂—CH=CH—CH₂ | H | H | CH₃ | CH |
| B.166 | C₆H₅—CH₂—CH=CH—CH₂ | H | H | CH₃ | N |
| B.167 | 4-F—C₆H₄—CH=CHCH₂ | H | H | CH₃ | CH |
| B.168 | 4-F—C₆H₄—CH=CHCH₂ | H | H | CH₃ | N |
| B.169 | t-C₄—H₉O—CO—CH₂ | H | H | CH₃ | CH |
| B.170 | t-C₄—H₉O—CO—CH₂ | H | H | CH₃ | N |
| B.171 | t-C₄—H₉O—CO—(CH₂)₃ | H | H | CH₃ | CH |
| B.172 | t-C₄—H₉O—CO—(CH₂)₃ | H | H | CH₃ | N |
| B.173 | Cl—CH=CH—CH₂ | H | H | CH₃ | CH |
| B.174 | Cl—CH=CH—CH₂ | H | H | CH₃ | N |
| B.175 | C₂H₅ | 6-OC₂H₅ | H | CH₃ | CH |
| B.176 | C₂H₅ | 6-OC₂H₅ | H | CH₃ | N |
| B.177 | CH₃—C(CH₃)₂ | H | H | CH₃ | CH |
| B.178 | CH₃—C(CH₃)₂ | H | H | CH₃ | N |
| B.179 | CH₃—CH(CH₃)—CH₂ | H | H | CH₃ | CH |
| B.180 | CH₃—CH(CH₃)—CH₂ | H | H | CH₃ | N |
| B.181 | CH₂=C(CH₃)—CH₂ | H | H | CH₃ | CH |
| B.182 | CH₂=C(CH₃)—CH₂ | H | H | CH₃ | N |
| B.183 | CH₃—CH(CH₃)—CH₂CH₂ | H | H | CH₃ | CH |
| B.184 | CH₃—CH(CH₃)—CH₂CH₂ | H | H | CH₃ | N |
| B.185 | CH₃—(CH₂)₄ | H | H | CH₃ | CH |
| B.186 | CH₃—(CH₂)₄ | H | H | CH₃ | N |
| B.187 | 2-F—C₆H₄—CH₂ | H | H | CH₃ | CH |
| B.188 | 2-F—C₆H₄—CH₂ | H | H | CH₃ | N |
| B.189 | 3-F—C₆H₄—CH₂ | H | H | CH₃ | CH |
| B.190 | 3-F—C₆H₄—CH₂ | H | H | CH₃ | N |

TABLE B-continued

| Comp. no. | R¹ | R² | R³ | R⁴ | X |
|---|---|---|---|---|---|
| B.191 | 2-Cl—C₆H₄—CH₂ | H | H | CH₃ | CH |
| B.192 | 2-Cl—C₆H₄—CH₂ | H | H | CH₃ | N |
| B.193 | 3,4-Cl₂—C₆H₃—CH₂ | H | H | CH₃ | CH |
| B.194 | 3,4-Cl₂—C₆H₃—CH₂ | H | H | CH₃ | N |
| B.195 | 2,6-Cl₂—C₆H₃—CH₂ | H | H | CH₃ | CH |
| B.196 | 2,6-Cl₂—C₆H₃—CH₂ | H | H | CH₃ | N |
| B.197 | C₆H₅—CH₂—CH₂ | H | H | CH₃ | CH |
| B.198 | C₆H₅—CH₂—CH₂ | H | H | CH₃ | N |
| B.199 | C₆H₅—CH=CH—CH₂—CH₂ | H | H | CH₃ | CH |
| B.200 | C₆H₅—CH=CH—CH₂—CH₂ | H | H | CH₃ | N |
| B.201 | 4-Cl—C₆H₄—CH₂—CH=CH—CH₂ | H | H | CH₃ | CH |
| B.202 | 4-Cl—C₆H₄—CH₂—CH=CH—CH₂ | H | H | CH₃ | N |
| B.203 | 4-CF₃—C₆H₄—CH₂—CH=CH—CH₂ | H | H | CH₃ | CH |
| B.204 | 4-CF₃—C₆H₄—CH₂—CH=CH—CH₂ | H | H | CH₃ | N |
| B.205 | CH₃ | H | H | C₆H₅ | CH |
| B.206 | CH₃ | H | H | CH₃ | N |
| B.207 | C₂H₅ | H | H | CH₃ | CH |
| B.208 | C₂H₅ | H | H | CH₃ | N |
| B.209 | CH₃—CH₂—CH₂ | H | H | CH₃ | CH |
| B.210 | CH₃—CH₂—CH₂ | H | H | CH₃ | N |
| B.211 | CH₃—(CH₂)₅ | H | H | CH₃ | CH |
| B.212 | CH₃—(CH₂)₅ | H | H | CH₃ | N |
| B.213 | C₆H₅—CH₂ | H | H | CH₃ | CH |
| B.214 | C₆H₅—CH₂ | H | H | CH₃ | N |
| B.215 | CH₃ | 2-CH₃ | 5-CH₃ | CH₃ | N |
| B.216 | CH₃ | 2-CH₃ | H | C₂H₅ | N |
| B.217 | CH₂=CH—CH₂ | 2-CH₃ | H | CH₃ | N |
| B.218 | C₂H₅ | 2-CH₃ | 5-CH₃ | CH₃ | N |
| B.219 | CH₂=CH—CH₂ | 2-CH₃ | H | CH₃ | CH |
| B.220 | CH₃—CH₂—CH₂ | 2-CH₃ | H | CH₃ | CH |
| B.221 | CH₃—CH₂—CH₂ | 2-CH₃ | H | CH₃ | N |
| B.222 | CH₃—CH(CH₃) | 2-CH₃ | H | CH₃ | CH |
| B.223 | CH₃—CH(CH₃) | 2-CH₃ | H | CH₃ | N |
| B.224 | CH₃—CH(CH₃)—CH₂ | 2-CH₃ | H | CH₃ | CH |
| B.225 | CH₃—CH(CH₃)—CH₂ | 2-CH₃ | H | CH₃ | N |
| B.226 | CH₃—(CH₂)₃ | 2-CH₃ | H | CH₃ | CH |
| B.227 | CH₃—(CH₂)₃ | 2-CH₃ | H | CH₃ | N |
| B.228 | CH₃—C(CH₃)₂ | 2-CH₃ | H | CH₃ | CH |
| B.229 | CH₃—C(CH₃)₂ | 2-CH₃ | H | CH₃ | N |
| B.230 | CH₂=C(CH₃)—CH₂ | 2-CH₃ | H | CH₃ | CH |
| B.231 | CH₂=C(CH₃)—CH₂ | 2-CH₃ | H | CH₃ | N |
| B.232 | CH₃—CH(CH₃)—CH₂CH₂ | 2-CH₃ | H | CH₃ | CH |
| B.233 | CH₃—CH(CH₃)—CH₂CH₂ | 2-CH₃ | H | CH₃ | N |
| B.234 | CH₃—(CH₂)₅ | 2-CH₃ | H | CH₃ | CH |
| B.235 | CH₃—(CH₂)₅ | 2-CH₃ | H | CH₃ | N |
| B.236 | C₆H₅—CH₂ | 2-CH₃ | H | CH₃ | CH |
| B.237 | C₆H₅—CH₂ | 2-CH₃ | H | CH₃ | N |
| B.238 | CH₃ | 2-CH₃ | 5-CH₃ | CH₃ | CH |
| B.239 | CH₂=CH—CH₂ | 2-CH₃ | 5-CH₃ | CH₃ | N |
| B.240 | CH₂=CH—CH₂ | 2-CH₃ | 5-CH₃ | CH₃ | CH |
| B.241 | CH₃—CH(CH₃) | 2-CH₃ | 5-CH₃ | CH₃ | N |
| B.242 | CH₃—CH(CH₃) | 2-CH₃ | 5-CH₃ | CH₃ | CH |
| B.243 | CH₃—(CH₂)₃ | 2-CH₃ | 5-CH₃ | CH₃ | N |
| B.244 | CH₃—(CH₂)₃ | 2-CH₃ | 5-CH₃ | CH₃ | CH |
| B.245 | C₆H₅—CH₂ | 2-CH₃ | 5-CH₃ | CH₃ | CH |
| B.246 | C₆H₅—CH₂ | 2-CH₃ | 5-CH₃ | CH₃ | N |
| B.247 | CH₃ | 3-CH₃C(CH₃)₂ | H | CH₃ | CH |
| B.248 | CH₃ | 3-CH₃C(CH₃)₂ | H | CH₃ | N |
| B.249 | CH₃ | 2-CH₃ | H | CH₃—CH₂ | CH |
| B.250 | CH₃ | 2-CH₃ | H | CH₃—CH₂ | N |
| B.251 | CH₂=CH—CH₂ | 2-CH₃ | H | CH₃—CH₂ | CH |
| B.252 | CH₂=CH—CH₂ | 2-CH₃ | H | CH₃—CH₂ | N |
| B.253 | CH₃—CH(CH₃) | 2-CH₃ | H | CH₃—CH₂ | CH |
| B.254 | CH₃—CH(CH₃) | 2-CH₃ | H | CH₃—CH₂ | N |
| B.255 | CH₃ | 2-CH₃ | H | CH₃—CH₂ | CH |
| B.256 | CH₃ | 2-CH₃ | H | CH₃—CH₂ | N |
| B.257 | CH₃ | 2-CH₃ | H | CH₃—CH₂—CH₂ | CH |
| B.258 | CH₃ | 2-CH₃ | H | CH₃—CH(CH₃) | N |
| B.259 | C₂H₅ | 2-CH₃ | 5-CH₃ | CH₃ | CH |
| B.260 | C₂H₅ | 2-CH₃ | H | C₂H₅ | CH |
| B.261 | C₂H₅ | 2-CH₃ | H | C₂H₅ | N |
| B.262 | CH₃—CH₂—CH₂ | 2-CH₃ | 5-CH₃ | CH₃ | CH |
| B.263 | CH₃—CH₂—CH₂ | 2-CH₃ | 5-CH₃ | CH₃ | N |
| B.264 | CH₃—CH₂—CH₂ | 2-CH₃ | H | C₂H₅ | CH |
| B.265 | CH₃—CH₂—CH₂ | 2-CH₃ | H | C₂H₅ | N |
| B.266 | CH₃ | 2-Cl | H | CH₃ | CH |

TABLE B-continued

| Comp. no. | R¹ | R² | R³ | R⁴ | X |
|---|---|---|---|---|---|
| B.267 | CH₃ | 2-Cl | H | CH₃ | N |
| B.268 | C₂H₅ | 2-Cl | H | CH₃ | CH |
| B.269 | C₂H₅ | 2-Cl | H | CH₃ | N |
| B.270 | CH₃ | 2-Cl | 5-CH₃ | CH₃ | CH |
| B.271 | CH₃ | 2-Cl | 5-CH₃ | CH₃ | N |
| B.272 | C₂H₅ | 2-Cl | 5-CH₃ | CH₃ | CH |
| B.273 | C₂H₅ | 2-Cl | 5-CH₃ | CH₃ | N |
| B.274 | CH₃ | 2-Cl | 5-Cl | CH₃ | CH |
| B.275 | CH₃ | 2-Cl | 5-Cl | CH₃ | N |
| B.276 | C₂H₅ | 2-Cl | 5-Cl | CH₃ | CH |
| B.277 | C₂H₅ | 2-Cl | 5-Cl | CH₃ | N |
| B.278 | CH₃—O—CH₂—CH₂ | 2-CH₃ | H | CH₃ | N |
| B.279 | CH₃—O—CH₂—CH₂ | 2-CH₃ | H | C₂H₅ | N |
| B.280 | CH₃—(CH₂)₃ | 2-CH₃ | H | C₂H₅ | N |
| B.281 | CH₃—O—CH₂—CH₂ | 2-CH₃ | 5-CH₃ | CH₃ | N |
| B.282 | CH₃ | 2-CH₃ | 5-CH₃ | C₂H₅ | N |
| B.283 | C₂H₅ | 2-CH₃ | 5-CH₃ | C₂H₅ | N |
| B.284 | CH₃—CH₂—CH₂ | 2-CH₃ | 5-CH₃ | C₂H₅ | N |
| B.285 | CH₂=CH—CH₂ | 2-CH₃ | 5-CH₃ | C₂H₅ | N |
| B.286 | CH₃—O—CH₂—CH₂ | 2-CH₃ | 5-CH₃ | C₂H₅ | N |
| B.287 | CH₃—(CH₂)₃ | 2-CH₃ | 5-CH₃ | C₂H₅ | N |
| B.288 | CH₃—CH₂—CH₂— | 2-Cl | H | CH₃ | N |
| B.289 | CH₃—CH₂—CH₂— | 2-Cl | H | CH₃ | CH |
| B.290 | CH₃—(CH₂)₃— | 2-Cl | H | CH₃ | N |
| B.291 | CH₃—(CH₂)₃— | 2-Cl | H | CH₃ | CH |
| B.292 | CH₂=CH—CH₂— | 2-Cl | H | CH₃ | N |
| B.293 | CH₂=CH—CH₂— | 2-Cl | H | CH₃ | CH |
| B.294 | CH₃—CH₂—CH₂— | 2-OCH₃ | H | CH₃ | N |
| B.295 | CH₃—CH₂—CH₂— | 2-OCH₃ | H | CH₃ | CH |
| B.296 | CH₃—(CH₂)₃— | 2-OCH₃ | H | CH₃ | N |
| B.297 | CH₃—(CH₂)₃— | 2-OCH₃ | H | CH₃ | CH |
| B.298 | CH₂=CH—CH₂— | 2-OCH₃ | H | CH₃ | N |
| B.299 | CH₂=CH—CH₂— | 2-OCH₃ | H | CH₃ | CH |
| B.300 | CH₃—CH₂—CH₂— | 3-CH₃ | H | CH₃ | N |
| B.301 | CH₃—CH₂—CH₂— | 3-CH₃ | H | CH₃ | CH |
| B.302 | CH₃—(CH₂)₃— | 3-CH₃ | H | CH₃ | N |
| B.303 | CH₃—(CH₂)₃— | 3-CH₃ | H | CH₃ | CH |
| B.304 | CH₂=CH—CH₂— | 3-CH₃ | H | CH₃ | N |
| B.305 | CH₂=CH—CH₂— | 3-CH₃ | H | CH₃ | CH |
| B.306 | CH₃ | 2-CH₃ | H | CH₃—CH₂—CH₂ | N |
| B.307 | CH₃ | 2-CH₃ | H | CH₃—CH₂—CH₂ | CH |
| B.308 | CH₃—(CH₂)₅— | 2-CH₃ | 5-CH₃ | CH₃ | N |
| B.309 | CH₃—(CH₂)₅— | 2-CH₃ | 5-CH₃ | CH₃ | CH |
| B.310 | CH≡C—CH₂— | 2-CH₃ | H | CH₃ | N |
| B.311 | CH≡C—CH₂— | 2-CH₃ | H | CH₃ | CH |
| B.312 | CH≡C—CH₂— | 2-CH₃ | H | CH₃—CH₂— | N |
| B.313 | CH≡C—CH₂— | 2-CH₃ | H | CH₃—CH₂— | CH |
| B.314 | CH≡C—CH₂— | 2-CH₃ | 5-CH₃ | CH₃ | N |
| B.315 | CH≡C—CH₂— | 2-CH₃ | 5-CH₃ | CH₃ | CH |
| B.316 | Cl—CH=CH—CH₂— | 2-CH₃ | H | CH₃ | N |
| B.317 | Cl—CH=CH—CH₂— | 2-CH₃ | H | CH₃ | CH |
| B.318 | Cl—CH=CH—CH₂— | 2-CH₃ | H | CH₃—CH₂— | N |
| B.319 | Cl—CH=CH—CH₂— | 2-CH₃ | H | CH₃—CH₂— | CH |
| B.320 | Cl—CH=CH—CH₂— | 2-CH₃ | 5-CH₃ | CH₃ | N |
| B.321 | Cl—CH=CH—CH₂— | 2-CH₃ | 5-CH₃ | CH₃ | CH |
| B.322 | N≡C—CH₂— | 2-CH₃ | H | CH₃ | N |
| B.323 | N≡C—CH₂— | 2-CH₃ | H | CH₃ | CH |
| B.324 | N≡C—CH₂— | 2-CH₃ | 5-CH₃ | CH₃ | N |
| B.325 | N≡C—CH₂— | 2-CH₃ | 5-CH₃ | CH₃ | CH |
| B.326 | CH₃ | 2-CH₃ | H | C₆H₅ | N |
| B.327 | CH₃ | 2-CH₃ | H | C₆H₅ | CH |
| B.328 | CH₃—CH₂—CH₂— | 2-CH₃ | H | C₆H₅ | N |
| B.329 | CH₃—CH₂—CH₂— | 2-CH₃ | H | C₆H₅ | CH |
| B.330 | (CH₃)₃COCO—CH₂— | 2-CH₃ | H | CH₃ | N |
| B.331 | (CH₃)₃COCO—CH₂— | 2-CH₃ | H | CH₃ | CH |
| B.332 | (CH₃)₃COCO—(CH₂)₃ | 2-CH₃ | H | CH₃ | N |
| B.333 | (CH₃)₃COCO—(CH₂)₃ | 2-CH₃ | H | CH₃ | CH |
| B.334 | (CH₃)₃COCO—(CH₂)₄ | 2-CH₃ | H | CH₃ | N |
| B.335 | (CH₃)₃COCO—(CH₂)₄ | 2-CH₃ | H | CH₃ | CH |
| B.336 | (CH₃)₃COCO—(CH₂)₅ | 2-CH₃ | H | CH₃ | N |
| B.337 | (CH₃)₃COCO—(CH₂)₅ | 2-CH₃ | H | CH₃ | CH |
| B.338 | CH≡C—CH₂— | 2-CH₃ | 5-CH₃ | CH₃—CH₂— | N |
| B.339 | CH≡C—CH₂— | 2-CH₃ | 5-CH₃ | CH₃—CH₂— | CH |
| B.340 | CH₃ | 2-F | H | CH₃ | N |
| B.341 | CH₃ | 2-F | H | CH₃ | CH |
| B.342 | CH₃—CH₂ | 2-F | H | CH₃ | N |
| B.343 | CH₃—CH₂ | 2-F | H | CH₃ | CH |
| B.344 | CH₃—CH₂—CH₂— | 2-F | H | CH₃ | N |
| B.345 | CH₃—CH₂—CH₂— | 2-F | H | CH₃ | CH |
| B.346 | CH₃—(CH₂)₃— | 2-F | H | CH₃ | N |

TABLE B-continued

| Comp. no. | R¹ | R² | R³ | R⁴ | X |
|---|---|---|---|---|---|
| B.347 | $CH_3-(CH_2)_3-$ | 2-F | H | $CH_3$ | CH |
| B.348 | $CH_2=CH-CH_2-$ | 2-F | H | $CH_3$ | N |
| B.349 | $CH_2=CH-CH_2-$ | 2-F | H | $CH_3$ | CH |
| B.350 | $CH_3-O-CH_2-CH_2-$ | 2-F | H | $CH_3$ | N |
| B.351 | $CH_3-O-CH_2-CH_2-$ | 2-F | H | $CH_3$ | CH |
| B.352 | $Cl-CH=CH-CH_2-$ | 2-F | H | $CH_3$ | N |
| B.353 | $Cl-CH=CH-CH_2-$ | 2-F | H | $CH_3$ | CH |
| B.354 | $CH_3$ | 2-F | H | $CH_3-CH_2-$ | N |
| B.355 | $CH_3$ | 2-F | H | $CH_3-CH_2-$ | CH |
| B.356 | $CH_3-CH_2$ | 2-F | H | $CH_3-CH_2-$ | N |
| B.357 | $CH_3-CH_2$ | 2-F | H | $CH_3-CH_2-$ | CH |
| B.358 | $CH_3-CH_2-CH_2$ | 2-F | H | $CH_3-CH_2-$ | N |
| B.359 | $CH_3-CH_2-CH_2$ | 2-F | H | $CH_3-CH_2-$ | CH |
| B.360 | $CH_3-(CH_2)_3-$ | 2-F | H | $CH_3-CH_2-$ | N |
| B.361 | $CH_3-(CH_2)_3-$ | 2-F | H | $CH_3-CH_2-$ | CH |
| B.362 | $CH_3-O-CH_2-CH_2-$ | 2-Cl | H | $CH_3$ | N |
| B.363 | $CH_3-O-CH_2-CH_2-$ | 2-Cl | H | $CH_3$ | CH |
| B.364 | $Cl-CH=CH-CH_2$ | 2-Cl | H | $CH_3$ | N |
| B.365 | $Cl-CH=CH-CH_2$ | 2-Cl | H | $CH_3$ | CH |
| B.366 | $CH_3$ | 2-Cl | H | $CH_3-CH_2-$ | N |
| B.367 | $CH_3$ | 2-Cl | H | $CH_3-CH_2-$ | CH |
| B.368 | $CH_3-CH_2-$ | 2-Cl | H | $CH_3-CH_2-$ | N |
| B.369 | $CH_3-CH_2-$ | 2-Cl | H | $CH_3-CH_2-$ | CH |
| B.370 | $CH_3-CH_2-CH_2$ | 2-Cl | H | $CH_3-CH_2-$ | N |
| B.371 | $CH_3-CH_2-CH_2$ | 2-Cl | H | $CH_3-CH_2-$ | CH |
| B.372 | $CH_3-(CH_2)_3-$ | 2-Cl | H | $CH_3-CH_2-$ | N |
| B.373 | $CH_3-(CH_2)_3-$ | 2-Cl | H | $CH_3-CH_2-$ | CH |
| B.374 | $CH_3$ | 2-Br | H | $CH_3$ | N |
| B.375 | $CH_3$ | 2-Br | H | $CH_3$ | CH |
| B.376 | $CH_3-CH_2$ | 2-Br | H | $CH_3$ | N |
| B.377 | $CH_3-CH_2$ | 2-Br | H | $CH_3$ | CH |
| B.378 | $CH_3-CH_2-CH_2$ | 2-Br | H | $CH_3$ | N |
| B.379 | $CH_3-CH_2-CH_2$ | 2-Br | H | $CH_3$ | CH |
| B.380 | $CH_3-(CH_2)_3-$ | 2-Br | H | $CH_3$ | N |
| B.381 | $CH_3-(CH_2)_3-$ | 2-Br | H | $CH_3$ | CH |
| B.382 | $CH_2=CH-CH_2-$ | 2-Br | H | $CH_3$ | N |
| B.383 | $CH_2=CH-CH_2-$ | 2-Br | H | $CH_3$ | CH |
| B.384 | $CH_3-O-CH_2-CH_2-$ | 2-Br | H | $CH_3$ | N |
| B.385 | $CH_3-O-CH_2-CH_2-$ | 2-Br | H | $CH_3$ | CH |
| B.386 | $Cl-CH=CH-CH_2-$ | 2-Br | H | $CH_3$ | N |
| B.387 | $Cl-CH=CH-CH_2-$ | 2-Br | H | $CH_3$ | CH |
| B.388 | $CH_3$ | 2-Br | H | $CH_3-CH_2-$ | N |
| B.389 | $CH_3$ | 2-Br | H | $CH_3-CH_2-$ | CH |
| B.390 | $CH_3-CH_2$ | 2-Br | H | $CH_3-CH_2-$ | N |
| B.391 | $CH_3-CH_2$ | 2-Br | H | $CH_3-CH_2-$ | CH |
| B.392 | $CH_3-CH_2-CH_2$ | 2-Br | H | $CH_3-CH_2-$ | N |
| B.393 | $CH_3-CH_2-CH_2$ | 2-Br | H | $CH_3-CH_2-$ | CH |
| B.394 | $CH_3-(CH_2)_3-$ | 2-Br | H | $CH_3-CH_2-$ | N |
| B.395 | $CH_3-(CH_2)_3-$ | 2-Br | H | $CH_3-CH_2-$ | CH |
| B.396 | $CH_3$ | 2-I | H | $CH_3$ | N |
| B.397 | $CH_3$ | 2-I | H | $CH_3$ | CH |
| B.398 | $CH_3-CH_2-$ | 2-I | H | $CH_3$ | N |
| B.399 | $CH_3-CH_2-$ | 2-I | H | $CH_3$ | CH |
| B.400 | $CH_3-CH_2-CH_2$ | 2-I | H | $CH_3$ | N |
| B.401 | $CH_3-CH_2-CH_2$ | 2-I | H | $CH_3$ | CH |
| B.402 | $CH_3-(CH_2)_3-$ | 2-I | H | $CH_3$ | N |
| B.403 | $CH_3-(CH_2)_3-$ | 2-I | H | $CH_3$ | CH |
| B.404 | $CH_2=CH-CH_2-$ | 2-I | H | $CH_3$ | N |
| B.405 | $CH_2=CH-CH_2-$ | 2-I | H | $CH_3$ | CH |
| B.406 | $CH_3-O-CH_2-CH_2-$ | 2-I | H | $CH_3$ | N |
| B.407 | $CH_3-O-CH_2-CH_2-$ | 2-I | H | $CH_3$ | CH |
| B.408 | $Cl-CH=CH-CH_2-$ | 2-I | H | $CH_3$ | N |
| B.409 | $Cl-CH=CH-CH_2-$ | 2-I | H | $CH_3$ | CH |
| B.410 | $CH_3$ | 2-I | H | $CH_3-CH_2-$ | N |
| B.411 | $CH_3$ | 2-I | H | $CH_3-CH_2-$ | CH |
| B.412 | $CH_3-CH_2$ | 2-I | H | $CH_3-CH_2-$ | N |
| B.413 | $CH_3-CH_2$ | 2-I | H | $CH_3-CH_2-$ | CH |
| B.414 | $CH_3-CH_2-CH_2$ | 2-I | H | $CH_3-CH_2-$ | N |
| B.415 | $CH_3-CH_2-CH_2$ | 2-I | H | $CH_3-CH_2-$ | CH |
| B.416 | $CH_3-(CH_2)_3-$ | 2-I | H | $CH_3-CH_2-$ | N |
| B.417 | $CH_3-(CH_2)_3-$ | 2-I | H | $CH_3-CH_2-$ | CH |
| B.418 | $CH_3$ | 2-$CH_3-CH_2-$ | H | $CH_3$ | N |
| B.419 | $CH_3$ | 2-$CH_3-CH_2-$ | H | $CH_3$ | CH |
| B.420 | $CH_3-CH_2-$ | 2-$CH_3-CH_2-$ | H | $CH_3$ | N |
| B.421 | $CH_3-CH_2-$ | 2-$CH_3-CH_2-$ | H | $CH_3$ | CH |
| B.422 | $CH_3-CH_2-CH_2$ | 2-$CH_3-CH_2-$ | H | $CH_3$ | N |
| B.423 | $CH_3-CH_2-CH_2$ | 2-$CH_3-CH_2-$ | H | $CH_3$ | CH |
| B.424 | $CH_3-(CH_2)_3-$ | 2-$CH_3-CH_2-$ | H | $CH_3$ | N |
| B.425 | $CH_3-(CH_2)_3-$ | 2-$CH_3-CH_2-$ | H | $CH_3$ | CH |
| B.426 | $CH_2=CH-CH_2-$ | 2-$CH_3-CH_2-$ | H | $CH_3$ | N |

TABLE B-continued

| Comp. no. | R¹ | R² | R³ | R⁴ | X |
|---|---|---|---|---|---|
| B.427 | CH$_2$=CH—CH$_2$— | 2-CH$_3$—CH$_2$— | H | CH$_3$ | CH |
| B.428 | CH$_3$—O—CH$_2$—CH$_2$— | 2-CH$_3$—CH$_2$— | H | CH$_3$ | N |
| B.429 | CH$_3$—O—CH$_2$—CH$_2$— | 2-CH$_3$—CH$_2$— | H | CH$_3$ | CH |
| B.430 | Cl—CH=CH—CH$_2$— | 2-CH$_3$—CH$_2$— | H | CH$_3$ | N |
| B.431 | Cl—CH=CH—CH$_2$— | 2-CH$_3$—CH$_2$— | H | CH$_3$ | CH |
| B.432 | CH$_3$ | 2-CH$_3$—CH$_2$— | H | CH$_3$—CH$_2$— | N |
| B.433 | CH$_3$ | 2-CH$_3$—CH$_2$— | H | CH$_3$—CH$_2$— | CH |
| B.434 | CH$_3$—CH$_2$ | 2-CH$_3$—CH$_2$— | H | CH$_3$—CH$_2$— | N |
| B.435 | CH$_3$—CH$_2$ | 2-CH$_3$—CH$_2$— | H | CH$_3$—CH$_2$— | CH |
| B.436 | CH$_3$—CH$_2$—CH$_2$ | 2-CH$_3$—CH$_2$— | H | CH$_3$—CH$_2$— | N |
| B.437 | CH$_3$—CH$_2$—CH$_2$ | 2-CH$_3$—CH$_2$— | H | CH$_3$—CH$_2$— | CH |
| B.438 | CH$_3$—(CH$_2$)$_3$— | 2-CH$_3$—CH$_2$— | H | CH$_3$—CH$_2$— | N |
| B.439 | CH$_3$—(CH$_2$)$_3$— | 2-CH$_3$—CH$_2$— | H | CH$_3$—CH$_2$— | CH |
| B.440 | CH$_3$—O—CH$_2$—CH$_2$— | 3-CH$_3$ | H | CH$_3$ | N |
| B.441 | CH$_3$—O—CH$_2$—CH$_2$— | 3-CH$_3$ | H | CH$_3$ | CH |
| B.442 | Cl—CH=CH—CH$_2$ | 3-CH$_3$ | H | CH$_3$ | N |
| B.443 | Cl—CH=CH—CH$_2$ | 3-CH$_3$ | H | CH$_3$ | CH |
| B.444 | CH$_3$ | 3-CH$_3$ | H | CH$_3$—CH$_2$— | N |
| B.445 | CH$_3$ | 3-CH$_3$ | H | CH$_3$—CH$_2$— | CH |
| B.446 | CH$_3$—CH$_2$ | 3-CH$_3$ | H | CH$_3$—CH$_2$— | N |
| B.447 | CH$_3$—CH$_2$ | 3-CH$_3$ | H | CH$_3$—CH$_2$— | CH |
| B.448 | CH$_3$—CH$_2$—CH$_2$ | 3-CH$_3$ | H | CH$_3$—CH$_2$— | N |
| B.449 | CH$_3$—CH$_2$—CH$_2$ | 3-CH$_3$ | H | CH$_3$—CH$_2$— | CH |
| B.450 | CH$_3$—(CH$_2$)$_3$— | 3-CH$_3$ | H | CH$_3$—CH$_2$— | N |
| B.451 | CH$_3$—(CH$_2$)$_3$— | 3-CH$_3$ | H | CH$_3$—CH$_2$— | CH |
| B.452 | CH$_3$—O—CH$_2$—CH$_2$— | 2-OCH$_3$ | H | CH$_3$ | N |
| B.453 | CH$_3$—O—CH$_2$—CH$_2$— | 2-OCH$_3$ | H | CH$_3$ | CH |
| B.454 | Cl—CH=CH—CH$_2$— | 2-OCH$_3$ | H | CH$_3$ | N |
| B.455 | Cl—CH=CH—CH$_2$— | 2-OCH$_3$ | H | CH$_3$ | CH |
| B.456 | CH$_3$ | 2-OCH$_3$ | H | CH$_3$—CH$_2$— | N |
| B.457 | CH$_3$ | 2-OCH$_3$ | H | CH$_3$—CH$_2$— | CH |
| B.458 | CH$_3$—CH$_2$— | 2-OCH$_3$ | H | CH$_3$—CH$_2$— | N |
| B.459 | CH$_3$—CH$_2$— | 2-OCH$_3$ | H | CH$_3$—CH$_2$— | CH |
| B.460 | CH$_3$—CH$_2$—CH$_2$ | 2-OCH$_3$ | H | CH$_3$—CH$_2$— | N |
| B.461 | CH$_3$—CH$_2$—CH$_2$ | 2-OCH$_3$ | H | CH$_3$—CH$_2$— | CH |
| B.462 | CH$_3$—(CH$_2$)$_3$— | 2-OCH$_3$ | H | CH$_3$—CH$_2$— | N |
| B.463 | CH$_3$—(CH$_2$)$_3$— | 2-OCH$_3$ | H | CH$_3$—CH$_2$— | CH |
| B.464 | CH$_3$ | 2-CN | H | CH$_3$ | N |
| B.465 | CH$_3$ | 2-CN | H | CH$_3$ | CH |
| B.466 | CH$_3$—CH$_2$ | 2-CN | H | CH$_3$ | N |
| B.467 | CH$_3$—CH$_2$ | 2-CN | H | CH$_3$ | CH |
| B.468 | CH$_3$—CH$_2$—CH$_2$ | 2-CN | H | CH$_3$ | N |
| B.469 | CH$_3$—CH$_2$—CH$_2$ | 2-CN | H | CH$_3$ | CH |
| B.470 | CH$_3$—(CH$_2$)$_3$— | 2-CN | H | CH$_3$ | N |
| B.471 | CH$_3$—(CH$_2$)$_3$— | 2-CN | H | CH$_3$ | CH |
| B.472 | CH$_2$=CH—CH$_2$— | 2-CN | H | CH$_3$ | N |
| B.473 | CH$_2$=CH—CH$_2$— | 2-CN | H | CH$_3$ | CH |
| B.474 | CH$_3$—O—CH$_2$—CH$_2$— | 2-CN | H | CH$_3$ | N |
| B.475 | CH$_3$—O—CH$_2$—CH$_2$— | 2-CN | H | CH$_3$ | CH |
| B.476 | Cl—CH=CH—CH$_2$— | 2-CN | H | CH$_3$ | N |
| B.477 | Cl—CH=CH—CH$_2$— | 2-CN | H | CH$_3$ | CH |
| B.478 | CH$_3$ | 2-CN | H | CH$_3$—CH$_2$— | N |
| B.479 | CH$_3$ | 2-CN | H | CH$_3$—CH$_2$— | CH |
| B.480 | CH$_3$—CH$_2$ | 2-CN | H | CH$_3$—CH$_2$— | N |
| B.481 | CH$_3$—CH$_2$ | 2-CN | H | CH$_3$—CH$_2$— | CH |
| B.482 | CH$_3$—CH$_2$—CH$_2$ | 2-CN | H | CH$_3$—CH$_2$— | N |
| B.483 | CH$_3$—CH$_2$—CH$_2$ | 2-CN | H | CH$_3$—CH$_2$— | CH |
| B.484 | CH$_3$—(CH$_2$)$_3$— | 2-CN | H | CH$_3$—CH$_2$— | N |
| B.485 | CH$_3$—(CH$_2$)$_3$— | 2-CN | H | CH$_3$—CH$_2$— | CH |
| B.486 | CH$_3$ | 2-NO$_2$ | H | CH$_3$ | N |
| B.487 | CH$_3$ | 2-NO$_2$ | H | CH$_3$ | CH |
| B.488 | CH$_3$—CH$_2$ | 2-NO$_2$ | H | CH$_3$ | N |
| B.489 | CH$_3$—CH$_2$ | 2-NO$_2$ | H | CH$_3$ | CH |
| B.490 | CH$_3$—CH$_2$—CH$_2$ | 2-NO$_2$ | H | CH$_3$ | N |
| B.491 | CH$_3$—CH$_2$—CH$_2$ | 2-NO$_2$ | H | CH$_3$ | CH |
| B.492 | CH$_3$—(CH$_2$)$_3$— | 2-NO$_2$ | H | CH$_3$ | N |
| B.493 | CH$_3$—(CH$_2$)$_3$— | 2-NO$_2$ | H | CH$_3$ | CH |
| B.494 | CH$_2$=CH—CH$_2$— | 2-NO$_2$ | H | CH$_3$ | N |
| B.495 | CH$_2$=CH—CH$_2$— | 2-NO$_2$ | H | CH$_3$ | CH |
| B.496 | CH$_3$—O—CH$_2$—CH$_2$— | 2-NO$_2$ | H | CH$_3$ | N |
| B.497 | CH$_3$—O—CH$_2$—CH$_2$— | 2-NO$_2$ | H | CH$_3$ | CH |
| B.498 | Cl—CH=CH—CH$_2$— | 2-NO$_2$ | H | CH$_3$ | N |
| B.499 | Cl—CH=CH—CH$_2$— | 2-NO$_2$ | H | CH$_3$ | CH |
| B.500 | CH$_3$ | 2-NO$_2$ | H | CH$_3$—CH$_2$— | N |
| B.501 | CH$_3$ | 2-NO$_2$ | H | CH$_3$—CH$_2$— | CH |
| B.502 | CH$_3$—CH$_2$ | 2-NO$_2$ | H | CH$_3$—CH$_2$— | N |
| B.503 | CH$_3$—CH$_2$ | 2-NO$_2$ | H | CH$_3$—CH$_2$— | CH |
| B.504 | CH$_3$—CH$_2$—CH$_2$ | 2-NO$_2$ | H | CH$_3$—CH$_2$— | N |
| B.505 | CH$_3$—CH$_2$—CH$_2$ | 2-NO$_2$ | H | CH$_3$—CH$_2$— | CH |
| B.506 | CH$_3$—(CH$_2$)$_3$— | 2-NO$_2$ | H | CH$_3$—CH$_2$— | N |

TABLE B-continued

| Comp. no. | R¹ | R² | R³ | R⁴ | X |
|---|---|---|---|---|---|
| B.507 | CH₃—(CH₂)₃— | 2-NO₂ | H | CH₃—CH₂— | CH |
| B.508 | CH₃—CH₂—CH₂ | 2-Cl | 5-Cl | CH₃ | N |
| B.509 | CH₃—CH₂—CH₂ | 2-Cl | 5-Cl | CH₃ | CH |
| B.510 | CH₃—(CH₂)₃— | 2-Cl | 5-Cl | CH₃ | N |
| B.511 | CH₃—(CH₂)₃— | 2-Cl | 5-Cl | CH₃ | CH |
| B.512 | CH₂=CH—CH₂— | 2-Cl | 5-Cl | CH₃ | N |
| B.513 | CH₂=CH—CH₂— | 2-Cl | 5-Cl | CH₃ | CH |
| B.514 | CH₃—O—CH₂—CH₂— | 2-Cl | 5-Cl | CH₃ | N |
| B.515 | CH₃—O—CH₂—CH₂— | 2-Cl | 5-Cl | CH₃ | CH |
| B.516 | Cl—CH=CH—CH₂— | 2-Cl | 5-Cl | CH₃ | N |
| B.517 | Cl—CH=CH—CH₂— | 2-Cl | 5-Cl | CH₃ | CH |
| B.518 | CH₃ | 2-Cl | 5-Cl | CH₃—CH₂— | N |
| B.519 | CH₃ | 2-Cl | 5-Cl | CH₃—CH₂— | CH |
| B.520 | CH₃—CH₂ | 2-Cl | 5-Cl | CH₃—CH₂— | N |
| B.521 | CH₃—CH₂ | 2-Cl | 5-Cl | CH₃—CH₂— | CH |
| B.522 | CH₃—CH₂—CH₂ | 2-Cl | 5-Cl | CH₃—CH₂— | N |
| B.523 | CH₃—CH₂—CH₂ | 2-Cl | 5-Cl | CH₃—CH₂— | CH |
| B.524 | CH₃—(CH₂)₃— | 2-Cl | 5-Cl | CH₃—CH₂— | N |
| B.525 | CH₃—(CH₂)₃— | 2-Cl | 5-Cl | CH₃—CH₂— | CH |
| B.526 | CH₃—CH₂—CH₂ | 2-Cl | 5-CH₃ | CH₃ | N |
| B.527 | CH₃—CH₂—CH₂ | 2-Cl | 5-CH₃ | CH₃ | CH |
| B.528 | CH₃—(CH₂)₃— | 2-Cl | 5-CH₃ | CH₃ | N |
| B.529 | CH₃—(CH₂)₃— | 2-Cl | 5-CH₃ | CH₃ | CH |
| B.530 | CH₂=CH—CH₂— | 2-Cl | 5-CH₃ | CH₃ | N |
| B.531 | CH₂=CH—CH₂— | 2-Cl | 5-CH₃ | CH₃ | CH |
| B.532 | CH₃—O—CH₂—CH₂— | 2-Cl | 5-CH₃ | CH₃ | N |
| B.533 | CH₃—O—CH₂—CH₂— | 2-Cl | 5-CH₃ | CH₃ | CH |
| B.534 | Cl—CH=CH—CH₂— | 2-Cl | 5-CH₃ | CH₃ | N |
| B.535 | Cl—CH=CH—CH₂— | 2-Cl | 5-CH₃ | CH₃ | CH |
| B.536 | CH₃ | 2-Cl | 5-CH₃ | CH₃—CH₂— | N |
| B.537 | CH₃ | 2-Cl | 5-CH₃ | CH₃—CH₂— | CH |
| B.538 | CH₃—CH₂ | 2-Cl | 5-CH₃ | CH₃—CH₂— | N |
| B.539 | CH₃—CH₂ | 2-Cl | 5-CH₃ | CH₃—CH₂— | CH |
| B.540 | CH₃—CH₂—CH₂ | 2-Cl | 5-CH₃ | CH₃—CH₂— | N |
| B.541 | CH₃—CH₂—CH₂ | 2-Cl | 5-CH₃ | CH₃—CH₂— | CH |
| B.542 | CH₃—(CH₂)₃— | 2-Cl | 5-CH₃ | CH₃—CH₂— | N |
| B.543 | CH₃—(CH₂)₃— | 2-Cl | 5-CH₃ | CH₃—CH₂— | CH |
| B.544 | CH₃ | 2-CH₃ | 5-Cl | CH₃ | N |
| B.545 | CH₃ | 2-CH₃ | 5-Cl | CH₃ | CH |
| B.546 | CH₃—CH₂ | 2-CH₃ | 5-Cl | CH₃ | N |
| B.547 | CH₃—CH₂ | 2-CH₃ | 5-Cl | CH₃ | CH |
| B.548 | CH₃—CH₂—CH₂ | 2-CH₃ | 5-Cl | CH₃ | N |
| B.549 | CH₃—CH₂—CH₂ | 2-CH₃ | 5-Cl | CH₃ | CH |
| B.550 | CH₃—(CH₂)₃— | 2-CH₃ | 5-Cl | CH₃ | N |
| B.551 | CH₃—(CH₂)₃— | 2-CH₃ | 5-Cl | CH₃ | CH |
| B.552 | CH₂=CH—CH₂— | 2-CH₃ | 5-Cl | CH₃ | N |
| B.553 | CH₂=CH—CH₂— | 2-CH₃ | 5-Cl | CH₃ | CH |
| B.554 | CH₃—O—CH₂—CH₂— | 2-CH₃ | 5-Cl | CH₃ | N |
| B.555 | CH₃—O—CH₂—CH₂— | 2-CH₃ | 5-Cl | CH₃ | CH |
| B.556 | Cl—CH=CH—CH₂— | 2-CH₃ | 5-Cl | CH₃ | N |
| B.557 | Cl—CH=CH—CH₂— | 2-CH₃ | 5-Cl | CH₃ | CH |
| B.558 | CH₃ | 2-CH₃ | 5-Cl | CH₃—CH₂— | N |
| B.559 | CH₃ | 2-CH₃ | 5-Cl | CH₃—CH₂— | CH |
| B.560 | CH₃—CH₂ | 2-CH₃ | 5-Cl | CH₃—CH₂— | N |
| B.561 | CH₃—CH₂ | 2-CH₃ | 5-Cl | CH₃—CH₂— | CH |
| B.562 | CH₃—CH₂—CH₂ | 2-CH₃ | 5-Cl | CH₃—CH₂— | N |
| B.563 | CH₃—CH₂—CH₂ | 2-CH₃ | 5-Cl | CH₃—CH₂— | CH |
| B.564 | CH₃—(CH₂)₃— | 2-CH₃ | 5-Cl | CH₃—CH₂— | N |
| B.565 | CH₃—(CH₂)₃— | 2-CH₃ | 5-Cl | CH₃—CH₂— | CH |
| B.566 | CH₃ | 2-OCH₃ | 5-CH₃ | CH₃ | N |
| B.567 | CH₃ | 2-OCH₃ | 5-CH₃ | CH₃ | CH |
| B.568 | CH₃—CH₂ | 2-OCH₃ | 5-CH₃ | CH₃ | N |
| B.569 | CH₃—CH₂ | 2-OCH₃ | 5-CH₃ | CH₃ | CH |
| B.570 | CH₃—CH₂—CH₂ | 2-OCH₃ | 5-CH₃ | CH₃ | N |
| B.571 | CH₃—CH₂—CH₂ | 2-OCH₃ | 5-CH₃ | CH₃ | CH |
| B.572 | CH₃—(CH₂)₃— | 2-OCH₃ | 5-CH₃ | CH₃ | N |
| B.573 | CH₃—(CH₂)₃— | 2-OCH₃ | 5-CH₃ | CH₃ | CH |
| B.574 | CH₂=CH—CH₂— | 2-OCH₃ | 5-CH₃ | CH₃ | N |
| B.575 | CH₂=CH—CH₂— | 2-OCH₃ | 5-CH₃ | CH₃ | CH |
| B.576 | CH₃—O—CH₂—CH₂— | 2-OCH₃ | 5-CH₃ | CH₃ | N |
| B.577 | CH₃—O—CH₂—CH₂— | 2-OCH₃ | 5-CH₃ | CH₃ | CH |
| B.578 | Cl—CH=CH—CH₂— | 2-OCH₃ | 5-CH₃ | CH₃ | N |
| B.579 | Cl—CH=CH—CH₂— | 2-OCH₃ | 5-CH₃ | CH₃ | CH |
| B.580 | CH₃ | 2-OCH₃ | 5-CH₃ | CH₃—CH₂— | N |
| B.581 | CH₃ | 2-OCH₃ | 5-CH₃ | CH₃—CH₂— | CH |
| B.582 | CH₃—CH₂ | 2-OCH₃ | 5-CH₃ | CH₃—CH₂— | N |
| B.583 | CH₃—CH₂ | 2-OCH₃ | 5-CH₃ | CH₃—CH₂— | CH |
| B.584 | CH₃—CH₂—CH₂ | 2-OCH₃ | 5-CH₃ | CH₃—CH₂— | N |
| B.585 | CH₃—CH₂—CH₂ | 2-OCH₃ | 5-CH₃ | CH₃—CH₂— | CH |
| B.586 | CH₃—(CH₂)₃— | 2-OCH₃ | 5-CH₃ | CH₃—CH₂— | N |

TABLE B-continued

| Comp. no. | R¹ | R² | R³ | R⁴ | X |
|---|---|---|---|---|---|
| B.587 | $CH_3-(CH_2)_3-$ | 2-$OCH_3$ | 5-$CH_3$ | $CH_3-CH_2-$ | CH |
| B.588 | $CH_3$ | 2-$CH_3$ | 6-$CH_3$ | $CH_3$ | N |
| B.589 | $CH_3$ | 2-$CH_3$ | 6-$CH_3$ | $CH_3$ | CH |
| B.590 | $CH_3-CH_2$ | 2-$CH_3$ | 6-$CH_3$ | $CH_3$ | N |
| B.591 | $CH_3-CH_2$ | 2-$CH_3$ | 6-$CH_3$ | $CH_3$ | CH |
| B.592 | $CH_3-CH_2-CH_2$ | 2-$CH_3$ | 6-$CH_3$ | $CH_3$ | N |
| B.593 | $CH_3-CH_2-CH_2$ | 2-$CH_3$ | 6-$CH_3$ | $CH_3$ | CH |
| B.594 | $CH_3-(CH_2)_3-$ | 2-$CH_3$ | 6-$CH_3$ | $CH_3$ | N |
| B.595 | $CH_3-(CH_2)_3-$ | 2-$CH_3$ | 6-$CH_3$ | $CH_3$ | CH |
| B.596 | $CH_2=CH-CH_2-$ | 2-$CH_3$ | 6-$CH_3$ | $CH_3$ | N |
| B.597 | $CH_2=CH-CH_2-$ | 2-$CH_3$ | 6-$CH_3$ | $CH_3$ | CH |
| B.598 | $CH_3-O-CH_2-CH_2-$ | 2-$CH_3$ | 6-$CH_3$ | $CH_3$ | N |
| B.599 | $CH_3-O-CH_2-CH_2-$ | 2-$CH_3$ | 6-$CH_3$ | $CH_3$ | CH |
| B.600 | $Cl-CH=CH-CH_2-$ | 2-$CH_3$ | 6-$CH_3$ | $CH_3$ | N |
| B.601 | $Cl-CH=CH-CH_2-$ | 2-$CH_3$ | 6-$CH_3$ | $CH_3$ | CH |
| B.602 | $CH_3$ | 2-$CH_3$ | 6-$CH_3$ | $CH_3-CH_2-$ | N |
| B.603 | $CH_3$ | 2-$CH_3$ | 6-$CH_3$ | $CH_3-CH_2-$ | CH |
| B.604 | $CH_3-CH_2$ | 2-$CH_3$ | 6-$CH_3$ | $CH_3-CH_2-$ | N |
| B.605 | $CH_3-CH_2$ | 2-$CH_3$ | 6-$CH_3$ | $CH_3-CH_2-$ | CH |
| B.606 | $CH_3-CH_2-CH_2$ | 2-$CH_3$ | 6-$CH_3$ | $CH_3-CH_2-$ | N |
| B.607 | $CH_3-CH_2-CH_2$ | 2-$CH_3$ | 6-$CH_3$ | $CH_3-CH_2-$ | CH |
| B.608 | $CH_3-(CH_2)_3-$ | 2-$CH_3$ | 6-$CH_3$ | $CH_3-CH_2-$ | N |
| B.609 | $CH_3-(CH_2)_3-$ | 2-$CH_3$ | 6-$CH_3$ | $CH_3-CH_2-$ | CH |
| B.610 | $CH_3$ | 2-$CH_3$ | 5-$CH(CH_3)_2$ | $CH_3$ | N |
| B.611 | $CH_3$ | 2-$CH_3$ | 5-$CH(CH_3)_2$ | $CH_3$ | CH |
| B.612 | $CH_3-CH_2$ | 2-$CH_3$ | 5-$CH(CH_3)_2$ | $CH_3$ | N |
| B.613 | $CH_3-CH_2$ | 2-$CH_3$ | 5-$CH(CH_3)_2$ | $CH_3$ | CH |
| B.614 | $CH_3-CH_2-CH_2$ | 2-$CH_3$ | 5-$CH(CH_3)_2$ | $CH_3$ | N |
| B.615 | $CH_3-CH_2-CH_2$ | 2-$CH_3$ | 5-$CH(CH_3)_2$ | $CH_3$ | CH |
| B.616 | $CH_3-(CH_2)_3-$ | 2-$CH_3$ | 5-$CH(CH_3)_2$ | $CH_3$ | N |
| B.617 | $CH_3-(CH_2)_3-$ | 2-$CH_3$ | 5-$CH(CH_3)_2$ | $CH_3$ | CH |
| B.618 | $CH_2=CH-CH_2-$ | 2-$CH_3$ | 5-$CH(CH_3)_2$ | $CH_3$ | N |
| B.619 | $CH_2=CH-CH_2-$ | 2-$CH_3$ | 5-$CH(CH_3)_2$ | $CH_3$ | CH |
| B.620 | $CH_3-O-CH_2-CH_2-$ | 2-$CH_3$ | 5-$CH(CH_3)_2$ | $CH_3$ | N |
| B.621 | $CH_3-O-CH_2-CH_2-$ | 2-$CH_3$ | 5-$CH(CH_3)_2$ | $CH_3$ | CH |
| B.622 | $Cl-CH=CH-CH_2-$ | 2-$CH_3$ | 5-$CH(CH_3)_2$ | $CH_3$ | N |
| B.623 | $Cl-CH=CH-CH_2-$ | 2-$CH_3$ | 5-$CH(CH_3)_2$ | $CH_3$ | CH |
| B.624 | $CH_3$ | 2-$CH_3$ | 5-$CH(CH_3)_2$ | $CH_3-CH_2-$ | N |
| B.625 | $CH_3$ | 2-$CH_3$ | 5-$CH(CH_3)_2$ | $CH_3-CH_2-$ | CH |
| B.626 | $CH_3-CH_2$ | 2-$CH_3$ | 5-$CH(CH_3)_2$ | $CH_3-CH_2-$ | N |
| B.627 | $CH_3-CH_2$ | 2-$CH_3$ | 5-$CH(CH_3)_2$ | $CH_3-CH_2-$ | CH |
| B.628 | $CH_3-CH_2-CH_2$ | 2-$CH_3$ | 5-$CH(CH_3)_2$ | $CH_3-CH_2-$ | N |
| B.629 | $CH_3-CH_2-CH_2$ | 2-$CH_3$ | 5-$CH(CH_3)_2$ | $CH_3-CH_2-$ | CH |
| B.630 | $CH_3-(CH_2)_3-$ | 2-$CH_3$ | 5-$CH(CH_3)_2$ | $CH_3-CH_2-$ | N |
| B.631 | $CH_3-(CH_2)_3-$ | 2-$CH_3$ | 5-$CH(CH_3)_2$ | $CH_3-CH_2-$ | CH |

TABLE C

| Comp. no. | R¹ | R² | R³ | R⁴ | R⁵ | R⁶ | X |
|---|---|---|---|---|---|---|---|
| C.001 | $CH_3-$ | 2-$CH_3$ | H | $CH_3$ | $CH_3$ | $CH_3$ | N |
| C.002 | $CH_3-$ | 3-$CH_3$ | H | $CH_3$ | $CH_3$ | $CH_3$ | CH |
| C.003 | $CH_3-CH_2$ | 2-$CH_3$ | H | $CH_3$ | $CH_3$ | $CH_3$ | N |
| C.004 | $CH_3-CH_2$ | 2-$CH_3$ | H | $CH_3$ | $CH_3$ | $CH_3$ | CH |
| C.005 | $CH_3$ | 2-$CH_3$ | H | $CH_3$ | H | H | N |
| C.006 | $CH_3$ | 2-$CH_3$ | H | $CH_3$ | $CH_3$ | $CH_3$ | CH |
| C.007 | $CH_3$ | 2-$CH_3$ | H | $CH_3$ | H | $C_2H_5$ | N |
| C.008 | $CH_3$ | 2-$CH_3$ | H | $CH_3$ | H | $C_2H_5$ | CH |
| C.009 | $CH_3$ | 2-$CH_3$ | H | $CH_3$ | $CH_3$ | $C_2H_5$ | CH |

TABLE D

| Comp. no. | R¹ | R² | R³ | X |
|---|---|---|---|---|
| D.001 | $CH_3-$ | H | H | CH |
| D.002 | $CH_3-$ | H | H | N |
| D.003 | $CH_3-$ | 2-Cl | H | CH |
| D.004 | $CH_3-$ | 2-Cl | H | N |
| D.005 | $CH_3-$ | 2-$CH_3$ | H | CH |
| D.006 | $CH_3-$ | 2-$CH_3$ | H | N |
| D.007 | $CH_3-$ | 2-$OCH_3$ | H | CH |
| D.008 | $CH_3-$ | 2-$OCH_3$ | H | N |
| D.009 | $CH_3-$ | 3-Cl | H | CH |
| D.010 | $CH_3-$ | 3-Cl | H | N |
| D.011 | $CH_3-$ | 3-$CH_3$ | H | CH |
| D.012 | $CH_3-$ | 3-$CH_3$ | H | N |
| D.013 | $CH_3-$ | 3-$OCH_3$ | H | CH |
| D.014 | $CH_3-$ | 3-$OCH_3$ | H | N |
| D.015 | $CH_3-$ | 2-Cl | 6-Cl | CH |
| D.016 | $CH_3-$ | 2-Cl | 6-Cl | N |
| D.017 | $CH_3-CH_2-$ | H | H | CH |
| D.018 | $CH_3-CH_2-$ | H | H | N |
| D.019 | $CH_3-CH_2-$ | 2-Cl | H | CH |
| D.020 | $CH_3-CH_2-$ | 2-Cl | H | N |

TABLE D-continued

| Comp. no. | R¹ | R² | R³ | X |
|---|---|---|---|---|
| D.021 | CH₃—CH₂— | 2-CH₃ | H | CH |
| D.022 | CH₃—CH₂— | 2-CH₃ | H | N |
| D.023 | CH₃—CH₂— | 2-OCH₃ | H | CH |
| D.024 | CH₃—CH₂— | 2-OCH₃ | H | N |
| D.025 | CH₃—CH₂— | 3-Cl | H | CH |
| D.026 | CH₃—CH₂— | 3-Cl | H | N |
| D.027 | CH₃—CH₂— | 3-CH₃ | H | CH |
| D.028 | CH₃—CH₂— | 3-CH₃ | H | N |
| D.029 | CH₃—CH₂— | 3-OCH₃ | H | CH |
| D.030 | CH₃—CH₂— | 3-OCH₃ | H | N |
| D.031 | CH₃—CH₂— | 2-Cl | H | CH |
| D.032 | CH₃—CH₂— | 2-Cl | 6-Cl | N |
| D.033 | CH₃—CH₂—CH₂— | H | 6-Cl | CH |
| D.034 | CH₃—CH₂—CH₂— | H | H | N |
| D.035 | CH₂=CH—CH₂— | H | H | CH |
| D.036 | CH₂=CH—CH₂— | H | H | N |
| D.037 | CH₃—CH(CH₃)— | H | H | CH |
| D.038 | CH₃—CH(CH₃)— | H | H | N |
| D.039 | HC≡C—CH₂— | H | H | CH |
| D.040 | HC≡C—CH₂— | H | H | N |
| D.041 | cyclo-C₃H₅—CH₂— | H | H | CH |
| D.042 | cyclo-C₃H₅—CH₂— | H | H | N |
| D.043 | CH₃—CH₂—CH₂—CH₂— | H | H | CH |
| D.044 | CH₃—CH₂—CH₂—CH₂— | H | H | N |
| D.045 | CH₃—CH=CH—CH₂— | H | H | CH |
| D.046 | CH₃—CH=CH—CH₂— | H | H | N |
| D.047 | CH₃—(CH₂)₅— | H | H | CH |
| D.048 | CH₃—(CH₂)₅— | H | H | N |
| D.049 | cyclo-C₆H₁₁— | H | H | CH |
| D.050 | cyclo-C₆H₁₁— | H | H | N |
| D.051 | C₆H₅—CH₂— | H | H | CH |
| D.052 | C₆H₅—CH₂— | H | H | N |
| D.053 | 4-Cl-C₆H₄—CH₂— | H | H | CH |
| D.054 | 4-Cl-C₆H₄—CH₂— | H | H | N |
| D.055 | 3-CF₃—C₆H₄—CH₂— | H | H | CH |
| D.056 | 3-CF₃—C₆H₄—CH₂— | H | H | N |
| D.057 | 4-Cl—C₆H₄—CH₂— | H | H | CH |
| D.058 | 4-Cl—C₆H₄—CH₂— | H | H | N |
| D.059 | C₆H₅—CH₂—CH₂—CH₂— | H | H | CH |
| D.060 | C₆H₅—CH₂—CH₂—CH₂— | H | H | N |
| D.061 | C₆H₅—(CH₂)₄— | H | H | CH |
| D.062 | C₆H₅—(CH₂)₄— | H | H | N |
| D.063 | C₆H₅—CH₂—CH=CH—CH₂— | H | H | CH |
| D.064 | C₆H₅—CH₂—CH=CH—CH₂— | H | H | N |
| D.065 | 4-F—C₆H₄—CH=CH—CH₂—CH₂— | H | H | CH |
| D.066 | 4-F—C₆H₄—CH=CH—CH₂—CH₂— | H | H | N |
| D.067 | t-C₄H₉O—CO—CH₂— | H | H | CH |
| D.068 | t-C₄H₉O—CO—CH₂— | H | H | N |
| D.069 | t-C₄H₉O—CO—(CH₂)₃— | H | H | CH |
| D.070 | t-C₄H₉O—CO—(CH₂)₃— | H | H | N |
| D.071 | Cl—CH=CH—CH₂— | H | H | CH |
| D.072 | Cl—CH=CH—CH₂— | H | H | N |
| D.073 | C₂H₅ | 6-OC₂H₅ | H | CH |
| D.074 | C₂H₅ | 6-OC₂H₅ | H | N |
| D.075 | CH₃—C(CH₃)₂— | H | H | CH |
| D.076 | CH₃—C(CH₃)₂— | H | H | N |
| D.077 | CH₃—CH(CH₃)—CH₂— | H | H | CH |
| D.078 | CH₃—CH(CH₃)—CH₂— | H | H | N |
| D.079 | CH₂=C(CH₃)—CH₂— | H | H | CH |
| D.080 | CH₂=C(CH₃)—CH₂— | H | H | N |
| D.081 | CH₃—CH(CH₃)—CH₂—CH₂— | H | H | CH |
| D.082 | CH₃—CH(CH₃)—CH₂—CH₂— | H | H | N |
| D.083 | CH₃—(CH₂)₄— | H | H | CH |
| D.084 | CH₃—(CH₂)₄— | H | H | N |
| D.085 | 2-F—C₆H₄—CH₂— | H | H | CH |
| D.086 | 2-F—C₆H₄—CH₂— | H | H | N |
| D.087 | 3-F—C₆H₄—CH₂— | H | H | CH |
| D.088 | 3-F—C₆H₄—CH₂— | H | H | N |
| D.089 | 2-Cl—C₆H₄—CH₂— | H | H | CH |
| D.090 | 2-Cl—C₆H₄—CH₂— | H | H | N |
| D.091 | 3,4-Cl₂—C₆H₃—CH₂— | H | H | CH |
| D.092 | 3,4-Cl₂—C₆H₃—CH₂— | H | H | N |
| D.093 | 2,6-Cl₂—C₆H₃—CH₂— | H | H | CH |
| D.094 | 2,6-Cl₂—C₆H₃—CH₂— | H | H | N |
| D.095 | C₆H₅—CH₂—CH₂— | H | H | CH |
| D.096 | C₆H₅—CH₂—CH₂— | H | H | N |
| D.097 | C₆H₅—CH=CH—CH₂—CH₂— | H | H | CH |
| D.098 | C₆H₅—CH=CH—CH₂—CH₂— | H | H | N |
| D.099 | 4-Cl—C₆H₅—CH₂—CH=CH—CH₂— | H | H | CH |
| D.100 | 4-Cl—C₆H₅—CH₂—CH=CH—CH₂— | H | H | N |
| D.101 | 4-CF₃—C₆H₅—CH₂—CH=CH—CH₂— | H | H | CH |

TABLE D-continued

| Comp. no. | R¹ | R² | R³ | X |
|---|---|---|---|---|
| D.102 | 4-CF$_3$—C$_6$H$_5$—CH$_2$—CH=CH—CH$_2$— | H | H | N |

TABLE E

| Comp. no. | R¹ | R² | R³ |
|---|---|---|---|
| E.001 | CH$_3$ | 2-CH$_3$ | 5-CH$_3$ |
| E.002 | CH$_3$CH$_2$— | 2-CH$_3$ | 5-CH$_3$ |
| E.003 | CH$_3$CH$_2$CH$_2$— | 2-CH$_3$ | 5-CH$_3$ |
| E.004 | CH$_3$CH$_2$CH$_2$CH$_2$— | 2-CH$_3$ | 5-CH$_3$ |
| E.005 | HC≡C—CH$_2$— | 2-CH$_3$ | 5-CH$_3$ |
| E.006 | CH$_2$=CH—CH$_2$— | 2-CH$_3$ | 5-CH$_3$ |
| E.007 | CH$_3$—CH=CH—CH$_2$ | 2-CH$_3$ | 5-CH$_3$ |
| E.008 | C$_2$H$_5$—CH$_2$—CH$_2$— | 2-CH$_3$ | 5-CH$_3$ |
| E.009 | CH$_3$ | 2-CH$_3$ | 2-Cl |
| E.010 | CH$_3$CH$_2$— | 2-CH$_3$ | 2-Cl |
| E.011 | CH$_3$CH$_2$CH$_2$— | 2-CH$_3$ | 2-Cl |
| E.012 | CH$_3$CH$_2$CH$_2$CH$_2$— | 2-CH$_3$ | 2-Cl |
| E.013 | CH$_2$=CH—CH$_2$— | 2-CH$_3$ | 2-Cl |
| E.014 | CH$_2$H$_5$—CH$_2$—CH$_2$— | 2-CH$_3$ | 2-Cl |
| E.015 | CH$_3$ | 2-CH$_3$ | 5-isopropyl |
| E.016 | CH$_3$CH$_2$— | 2-CH$_3$ | 5-isopropyl |
| E.017 | CH$_3$CH$_2$CH$_2$— | 2-CH$_3$ | 5-isopropyl |
| E.018 | CH$_3$CH$_2$CH$_2$CH$_2$— | 2-CH$_3$ | 5-isopropyl |
| E.019 | CH$_2$=CH—CH$_2$— | 2-CH$_3$ | 5-isopropyl |
| E.020 | CH$_2$H$_5$—CH$_2$—CH$_2$— | 2-CH$_3$ | 5-isopropyl |
| E.021 | CH$_3$ | 2-Cl | 5-Cl |
| E.022 | CH$_3$CH$_2$— | 2-Cl | 5-Cl |
| E.023 | CH$_3$CH$_2$CH$_2$— | 2-Cl | 5-Cl |
| E.024 | CH$_3$CH$_2$CH$_2$CH$_2$— | 2-Cl | 5-Cl |
| E.025 | HC≡C—CH$_2$— | 2-Cl | 5-Cl |
| E.026 | CH$_2$=CH—CH$_2$— | 2-Cl | 5-Cl |
| E.027 | C$_2$H$_5$—CH$_2$—CH$_2$— | 2-Cl | 5-Cl |
| E.028 | CH$_3$ | 2-F | H |
| E.029 | CH$_3$CH$_2$— | 2-F | H |
| E.030 | CH$_3$CH$_2$CH$_2$— | 2-F | H |
| E.031 | CH$_3$CH$_2$CH$_2$CH$_2$— | 2-F | H |
| E.032 | HC≡C—CH$_2$— | 2-F | H |
| E.033 | CH$_2$=CH—CH$_2$— | 2-F | H |
| E.034 | CH$_3$ | 2-Cl | 5-CH$_3$ |
| E.035 | CH$_3$CH$_2$— | 2-Cl | 5-CH$_3$ |
| E.036 | CH$_3$CH$_2$CH$_2$— | 2-Cl | 5-CH$_3$ |
| E.037 | CH$_3$CH$_2$CH$_2$CH$_2$— | 2-Cl | 5-CH$_3$ |
| E.038 | HC≡C—CH$_2$— | 2-Cl | 5-CH$_3$ |
| E.039 | CH$_2$=CH—CH$_2$— | 2-Cl | 5-CH$_3$ |
| E.040 | CH$_3$ | 2-CN | H |
| E.041 | CH$_3$CH$_2$— | 2-CN | H |
| E.042 | CH$_3$(CH$_2$)$_4$— | 2-CH$_3$ | 5-CH$_3$ |
| E.043 | CH$_3$(CH$_2$)$_5$— | 2-CH$_3$ | 5-CH$_3$ |
| E.044 | C$_6$H$_5$—CH$_2$— | 2-CH$_3$ | 5-CH$_3$ |
| E.045 | t-C$_4$H$_9$O—CO—CH$_2$— | 2-CH$_3$ | 5-CH$_3$ |
| E.046 | Cl—CH=CH—CH$_2$— | 2-CH$_3$ | 5-CH$_3$ |
| E.047 | CH$_3$O—CH$_2$—CH$_2$— | 2-CH$_3$ | 5-CH$_3$ |
| E.048 | CH$_3$CH$_2$— | 2-CH$_3$ | H |
| E.049 | CH$_3$CH$_2$CH$_2$CH$_2$— | 2-CH$_3$ | H |
| E.050 | CH$_3$(CH$_2$)$_4$— | 2-CH$_3$ | H |
| E.051 | CH$_3$(CH$_2$)$_5$— | 2-CH$_3$ | H |
| E.052 | CH$_3$(CH$_2$)$_6$— | 2-CH$_3$ | H |
| E.053 | HC≡C—CH$_2$— | 2-CH$_3$ | H |
| E.054 | CH$_2$=CH—CH$_2$— | 2-CH$_3$ | H |
| E.055 | CH$_3$—CH=CH—CH$_2$— | 2-CH$_3$ | H |
| E.056 | C$_2$H$_5$—CH$_2$—CH$_2$— | 2-CH$_3$ | H |
| E.057 | CH$_3$O—CH$_2$—CH$_2$ | 2-CH$_3$ | H |
| E.058 | C$_6$H$_5$—CH$_2$— | 2-CH$_3$ | H |
| E.059 | Cl—CH=CH—CH$_2$— | 2-CH$_3$ | H |
| E.060 | t-C$_4$H$_9$O—CH—CH$_2$— | 2-CH$_3$ | H |
| E.061 | cyclo-C$_6$H$_{11}$— | 2-CH$_3$ | H |
| E.062 | (CH$_3$)$_2$—CH— | 2-CH$_3$ | H |
| E.063 | t-butyl- | 2-CH$_3$ | H |
| E.064 | (CH$_3$)$_2$—CH—CH$_2$— | 2-CH$_3$ | H |
| E.065 | (CH$_3$)$_2$—CH— | 2-CH$_3$ | 5-CH$_3$ |
| E.066 | t-butyl | 2-CH$_3$ | 5-CH$_3$ |
| E.067 | (CH$_3$)$_2$—CH—CH$_2$— | 2-CH$_3$ | 5-CH$_3$ |

In general terms, the novel compounds I are extremely effective on a broad spectrum of phytopathogenic fungi, in particular those from the class consisting of the Ascomycetes and Basidiomycetes. Some of them have a remarkably high systemic mobility and action after application to the soil and particularly to foliage.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia solani* in cotton,
*Ustilago* species in cereals and sugar cane,
*Venturia inaegualis* (scab) in apples,
*Helminthosporium* species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Fusarium* and *Verticillium* species in various plants,
*Plasmopara viticola* in grapes,
*Alternaria* species in fruit and vegetables.

The compounds I are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare,. depending on the type of effect desired.

When the active ingredients are used for treating seed, application rates of from 0.001 to 50, and preferably from 0.01 to 10, g per kg of seed are generally required.

When the agents according to the invention are used as fungicides, they may be employed together with other active ingredients, e.g., herbicides, insecticides, growth regulators, other fungicides and fertilizers.

When admixed with other fungicides, the spectrum of fungicidal action is in many instances increased.

The compounds of the formula IA are suitable for effectively combating pests such as insects, arachnids and nematodes. They may be used as pesticides in crop protection and in the hygiene, stores protection and veterinary sector.

Examples of injurious insects belonging to the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Hellothis virescens, Hellothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Phyacionia frustrana, Scrobipalpula absoluta, Sitotroga cerealella, Sparganothis pilleriana, Spodoptera irugiperda, Spodoptera littoralis, Spodoptera litura, Thaumatopoea pityocampa, Tortrix viridana, Trichoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibiaIls, Conoderus vespertinus, Crioceris asparagi, Diabrotica longicornis, Diabrotica 12-punctara, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthopophaga, Culex piplens, Dacus cucurbitae, Dacus oleae, Dasineura brassicae, Fannia canicularis, Gasterophilus intestinalis, Glossina morsitans, Haematobia irritans, Haplodiplosis eguestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hyoscyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor.*

Examples from the Homoptera order are *Acyrthosiphon onobrychis, Adelges laricis, Aphidula nasturtii, Aphis fabae, Aphis pomi, Aphis sambuci, Bemisia tabaci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophiumdirhodum, Myzodes persicae, Myzus cerasi, Nephotettix cincticeps, Nilaparvata lugens, Pemphigus bursarius, Perkinsiella saccharicida, Phorodon humuli, Psylla mali, Psylla piri, Rhopalomyzus ascalonicus, Rhopalosiphummaidis, Sappahis mali, Schizaphis graminum, Schizoneura lanuginosa, Trialeurodes vaporariorum* and *Viteus vitifolii.*

Examples from the Isoptera order are *Calotermes flavicollis, Leucotermes flavipes, Retuculitermes lucifugus* and *Termes natalensis.*

Examples from the Orthoptera order are *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus.*

Examples from the Acarina order are *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Metatetranychus (Panonychus) ulmi, Ornithodorus moubata, Otobins megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tet-*

*ranychus pacificus, Tetranychus telarius* and *Tetranychus urticae.*

Examples from the nematodes class are root-knot nematodes, e.g., *Meloidogyne hapla, Meloidogyne incognita, Meloidogyne javanica,* Zysten bildende Nematoden, z.B. *Globodera rostochiensis, Heterodera avenae, Heterodera glycinae, Heterodera schachtii, Heterodera trifolii,* Stock- und Blattalchen, z.B. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The active ingredient concentrations in the finished formulations may vary within wide limits, but are generally from 0.0001 to 10, and preferably from 0.01 to 1%.

The active ingredients may also be successfully used in the ultra-low-volume (ULV) method, where it is possible to apply formulations containing more than 95wt % of active ingredient, or the active ingredient without any additives at all.

When the active ingredients are used for combating pests in the open, the application rates are from 0.1 to 2.0, and preferably from 0.2 to 1.0, kg/ha.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal. and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

The formulations generally contain from 0.01 to 95, and preferably from 0.1 to 90, wt % of active ingredient. The active ingredients are used in a purity of from 90 to 100, and preferably from 95 to 100% (according to the NMR spectrum).

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of formulations are as follows:

Granules, e.g., coated, impregnated or homogeneous granules; they may be preparedby bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The active ingredients may also be applied together with other crop protection agents such as herbicides, fungicides other pesticides and bactericides. These agents may be added to the agents according to the invention in a weight ratio of from 1:10 to 10:1, if desired immediately prior to use (tankmix).

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

Examples demonstrating the action on injurious fungi

For comparison purposes the following compounds were used: 2-(2'-methylphenoxymethyl)-phenylglyoxylic acid methyl ester-O-methyloxime (A) having the formula

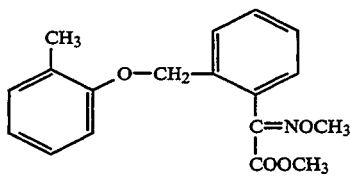

(disclosed in EP 253 213)

and 2-(2'-methyl-4'-(methoximinoeth-1''-yl)-phenoxymethyl)phenylglyoxylic acid methyl ester-O-methyloxime (B) having the formula

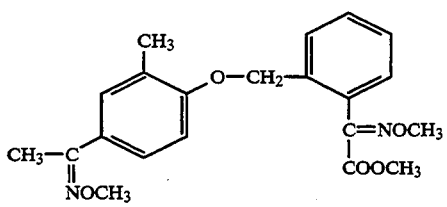

(disclosed in EP 386 561)

A.1 Action on Plasmopara

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

| Active ingredient no. | Percentage leaf attack after applying aqueous formulations containing ... ppm of active ingredient | |
|---|---|---|
| | 60 ppm | 15 ppm |
| I.007 | 0 | 0 |
| I.011 | 0 | 0 |
| Untreated | 65 | |

A.2 Action on wheat brown rust

Leaves of pot-grown wheat seedlings of the "Kanzler" variety were dusted with spores of brown rust (Puccinia recondita). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

| Active ingredient no. | Percentage leaf attack after application of aqueous formulations containing ... ppm of active ingredient | |
|---|---|---|
| | 60 ppm | 15 ppm |
| I.007 | 0 | 0 |
| I.011 | 0 | 0 |
| Untreated | 70 | |

A. 3 Action on bean rust

The undersides of leaves of bush beans of the "Fori" variety were uniformly sprayed with an aqueous spore suspension of bean rust (Uromyces appendiculatus). The plants were then kept for 24 hours in a high-humidity climatic cabinet at 19° C. and then set up in the greenhouse at 22° to 25° C. After 2 to 3 days the lower (basal) half of the upper side of the leaves was sprayed with the active ingredients. Fungus spread was assessed 10 to 12 days after spraying. As a result of the temporal and spatial separation of leaf treatment with the spores and leaf treatment with the active ingredients, there is no direct contact between fungus and active ingredient; consequently, the fungicidal action must have been preceded by active ingredient uptake and migration (systemic transport) in the leaf. By examining the various leaf zones it is possible to ascertain whether translaminar or apical movement of the candidate active ingredients has taken place in the leaf.

The results of the experiment show that, after treatment with a spray liquor containing 50 ppm of active ingredient, active ingredients nos. I.003, I.007 and I.014 had a fungicidal action on the leaf undersides and in part on the uncreated portion of the bean leaves, whereas the prior art comparative compounds A and B had no fungicidal action.

Use examples demonstrating the action on pests

The action of compounds of the general formula IA on pests from the class of insects, mites and nematodes may be demonstrated by the following experiments:

The active ingredients were formulated a) as a 0.1% strength solution in acetone, or b) as a 10% strength emulsion in a mixture of 70wt % of cyclohexanol, 20wt % of Nekanil ®LN (Lutenso ® AP6, a spreader-sticker with an emulsifying and dispersing action based on ethoxylaced alkylphenols) and 10wt % of EmulphorI EL (Emulan-®EL, an emulsifier based on ethoxylated fatty alcohols)

and diluted to the desired concentration with acetone in the case of a) and with water in the case of b).

Upon conclusion of the experiments the lowest concentration was determined at which the compounds, compared with the uncreated controls, achieved 80% inhibition or kill (action threshold or minimum concentration).

B.1 Aphis fabae, contact action

Bush beans (Vicia faba) under heavy louse attack were treated with aqueous formuations of the active ingredients.

The kill rate was determined after 24 hours.

In this test, compounds nos. I.007, I.011, I.015, I.003, I.001, I.017, I.058, I.086, I.096 and I.029 exhibited action thresholds of from 200 to 1000 ppm.

B.2 *Nephotettix cincticeps*, contact action

Circular filter papers were treated with aqueous formulations of the active ingredients; 5 adult leafhoppers were then placed on the filter papers.

the kill rate was determined after 24 hours.

In this test, compounds nos. I.007, I.011, I.014, I.015, I.003, I.002, I.004, I.017, I.117, I.307, I.192, I.193, I.195 and I.201 exhibited action thresholds of from 0.4 to 0.1 mg.

B.3 *Prodenia litura*, breeding experiment

Five caterpillars in the development stage L3 (10–12 mm) were placed on a standard nutrient medium (3.1 liters of water, 80 g of agar, 137 g of brewer's yeast, 515 g of cornflour, 130 g of wheat germ, and conventional additives and vitamins (20 g of Wessons salt, 5 g of Nipagin, 5 g of sorbic acid, 10 g of cellulose powder, 18 g of ascorbic acid, 1 g of Lutavit ® blend (vitamin) and 5 ml of alcoholic biotin solution)) which had previously been wetted with aqueous formulations of the active ingredients.

Observation extended up to emergence of the moths in a control experiment without active ingredient.

In this test, compounds nos. I.003, I.014, I.015, I.017, I.057, I.064, I.068, I.076, I.100, I.108, I.109, I.112, I.119 and I.079 exhibited action thresholds of from 200 to 0.1 ppm.

B.4 *Agrotis ypsilon*, contact action

Corn leaves were dipped for 3 seconds in aqueous formulations of the active ingredients and placed, after excess liquid had been allowed to drip off, on circular filter papers in a Petri dish 12 cm in diameter. 5 caterpillars in the third and fourth larval stages (about 15 mm long) were placed in each dish.

The action in % feeding inhibition and % kill was assessed after 24 and 48 hours.

In this test, compounds nos. I.060, I.070, I.086, I.090, I.096, I.117, I.121, I.129, I.140, I.177, I.307, I.189, I.190, I.191, I.192, I.193, I.195, I.201 and I.213 exhibited a threshold action of from 10 to 1000 ppm.

B.5 *Sitophilus granaria*, contact action

The bottoms of experimental vessels were treated with acetonic solutions of the active ingredients. After the acetone 10 had evaporated, about 50 weevils were introduced into each dish.

After 4 hours, the weevils were transferred to cardboard dishes, which were then placed in the experimental vessels.

The action was determined after 24 hours in percentage kill. Weevils unable to leave the cardboard dishes were considered to be dead or heavily damaged.

In this test, compound no. I.115 exhibited an action threshold of 1 mg.

B.6 *Musca domestica*, contact experiment

The bottoms of experimental vessels were wetted with acetonic solutions of the active ingredients and, after the solvent had evaporated, 10 flies were placed in each vessel.

The kill rate was determined after 4 hours.

In this test, compounds nos. I.064, I.071, I.077, I.078, I.080, I.083, I.085, I.098, I.100, I.103, I.106, I.111, I.115, I.117, I.126, I.127, I.130, I.133, I.309 and I.184 exhibited an action threshold of from 0.01 to 2 mg.

B.7 *Musca domestica*, breeding experiment 25 ml of a dry feed mix (1 kg of bran, 250 g of yeast powder, 35 g of fish meal) was mixed with the active ingredients and 25 ml of a milk-sugar solution (1 liter of milk and 42 g of sugar) and 20 larvae of the first development stage were then placed on it.

The kill rate was determined after the larvae in a control experiment had hatched.

In this test, compound no. I.064 exhibited an action threshold of 40 ppm.

B.8 *Prodenia litura*, contact experiment

Circular filter papers 9 cm in diameter were treated with 1 cm$^3$ of aqueous formulations of the active ingredients and then placed in a plastic Petri dish 94 mm in diamter. 5 Prodenia caterpillars L3 were then introduced into each dish and the dishes were closed. Assessment took place after 24 hours.

In this test, compounds nos. I.098, I.100, I.102, I.106, I.111, I.115 and I.184 exhibited an action theshold of from 0.1 to 1 mg.

B.9 *Prodenia litura*, breeding experiment

Five caterpillars in the development stage L3 (10–12 mm) were placed on a standard nutrient medium (3.1 liters of water, 80 g of agar, 137 g of brewer's yeast, 515 g of cornflour, 130 g of wheat germ, and conventional additives and vitamins (20 g of Wessons salt, 5 g of Nipagin, 5 g of sorbic acid, 10 g of cellulose powder, 18 g of ascorbic acid, 1 g of Lutavit ® blend (vitamin) and 5 ml of alcoholic biotin solution)) which had previously been wetted with aqueous formulations of the active ingredients.

Observation extended up to emergence of the moths in a control experiment without active ingredient.

In this test, compounds nos. I.128, I.272, I.292, I.293, I.307 and I.310 exhibited an action threshold of from 1 to 1000 ppm.

B.10 *Plutella maculipennis*, contact action

Leaves of young cabbage plants were wetted with aqueous solutions of the active ingredients and then placed on moistened filter papers. 10 caterpillars in the fourth development stage were then placed on the leaves prepared in this way.

The kill rate was determined after 48 hours.

In this test, compounds nos. I.064, I.065, I.068, I.079, I.081, I.084, I.086, I.088, I.090, I.117 and I.130 exhibited an action threshold of from 200 to 1000 ppm.

B.11 *Aedes aegypti*, breeding experiment

Plastic beakers 8 cm in diameter and holding 250 ml were filled with 200 ml of tapwater of 23° C.; 30–40 Aedes larvae in the third to fourth larval stage were then introduced into each beaker. The candidate compounds are then added as aqueous emulsions or suspensions to the vessels and the kill rate is determined after 24 hours. Breeding is then continued until the mosquitoes emerge. The room temperature is 25° C.

In this test, compound no. I.128 exhibited an action threshold of 0.1 ppm.

We claim:

1. A substituted oxime ether of the formula I

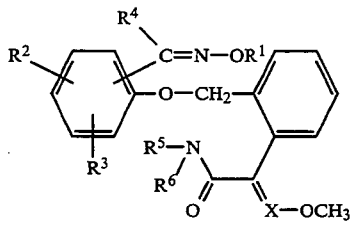

where

R$^1$ is C$_1$-C$_6$-alkyl, C$_3$-C$_6$-alkenyl, C$_3$-C$_4$-alkynyl, C$_1$-C$_6$-haloalkyl, C$_3$-C$_6$-haloalkenyl, C$_1$-C$_4$-alkoxy-C$_1$-C$_6$-alkyl, C$_3$-C$_6$-cycloalkyl, C$_3$-C$_6$-cycloalkyl-C$_1$-C$_4$-alkyl, cyano-C$_1$-C$_6$-alkyl, C$_1$-C$_6$-alkoxycarbonyl-C$_1$-C$_6$-alkyl, aryl-C$_1$-C$_6$-alkyl, hetaryl-C$_1$-C$_6$-alkyl, aryl-C$_3$-C$_6$-alkenyl or aryloxy-C$_1$-C$_6$-alkyl, where the aromatic or heteroaromatic ring is unsubstituted or substituted by one or more of the following radicals: C$_1$-C$_4$-alkyl, C$_1$- or C$_2$-haloalkyl, C$_3$-C$_6$-cycloalkyl, C$_1$-C$_4$-alkoxy, C$_1$ or C$_2$-haloalkoxy, halogen, aryl or aryloxy, R$^2$ and R$^3$ are identical or different and are each hydrogen, C$_1$-C$_4$-alkyl, C$_1$- or C$_2$-haloalkyl, C$_1$-C$_4$-alkoxy, C$_1$- or C$_2$-haloalkoxy, halogen, cyano or nitro, R$^4$ is hydrogen, C$_1$-C$_6$-alkyl, C$_3$-C$_6$-cycloalkyl, C$_1$-C$_2$-haloalkyl or aryl, where the aromatic ring is unsubstituted or substituted by one or more of the following radicals: C$_1$-C$_4$-alkyl, C$_1$- or C$_2$-haloalkyl, C$_1$-C$_4$-alkoxy, C$_1$- or C$_2$-haloalkoxy, halogen, cyano or nitro, R$^5$ and R$^6$ are identical or different and are each hydrogen or C$_1$-C$_4$-alkyl and X is CH or N.

2. A fungicidal composition comprising an inert carrier and a fungicidal amount of a substituted oxime ether of the formula I as claimed in claim 1.

3. A method for controlling fungi, wherein the fungi or the materials, plants or seeds threatened by fungal attack or the soil is or are treated with a fungicidal amount of a substituted oxime ether of the formula I as claimed in claim 1.

4. A pesticidal composition effective against insects, arachnids or nematodes comprising inert additives and a pesticidal amount of a compound of the formula I as claimed in claim 1.

5. A compound of the formula I as claimed in claim 1, where R$^1$, R$^2$ (in the 2-position), R$^4$ and R$^5$ are each methyl, R$^3$ and R$^5$ are each hydrogen, X is N and the oximinoethyl radical is in the 4-position.

6. A compound of the formula I as claimed in claim 1, where R$^1$, R$^2$ (in the 2-position), R$^4$ and R$^6$ are each methyl, R$^3$ and R$^5$ are each hydrogen, X is CH and the oximinoethyl radical is in the 4-position.

7. A compound of the formula I as claimed in claim 1, where R$^1$ is methyl, R$^2$ in the 2-position is methyl, R$^4$ is cyclopropyl, R$^6$ is methyl, R$^3$ and R$^5$ are each hydrogen, X is N and the oximino radical is in the 4-position.

8. A compound of the formula I as claimed in claim 1, where R$^1$ is methyl, R$^2$ in the 2-position is methyl, R$^4$ is trifluoromethyl, R$^6$ is methyl, R$^3$ and R$^5$ are each hydrogen, X is N and the oximino radical is in the 4-position.

* * * * *